(12) United States Patent
Kristen et al.

(10) Patent No.: US 6,900,278 B2
(45) Date of Patent: May 31, 2005

(54) LIGANDS, COMPLEX COMPOUNDS AND THEIR USE FOR POLYMERISING OLEFINS

(75) Inventors: Marc Oliver Kristen, Limburgerhof (DE); Benno Bildstein, Innsbruck (AT); Christoph Amort, Rodeneck (IT); Michael Malaun, Munich (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/312,587

(22) PCT Filed: Jul. 13, 2001

(86) PCT No.: PCT/EP01/08113

§ 371 (c)(1),
(2), (4) Date: Jan. 17, 2003

(87) PCT Pub. No.: WO02/08236

PCT Pub. Date: Jan. 31, 2002

(65) Prior Publication Data

US 2004/0030072 A1 Feb. 12, 2004

(30) Foreign Application Priority Data

Jul. 20, 2000 (DE) .......................................... 100 35 654

(51) Int. Cl.[7] .................................................. C08F 4/44
(52) U.S. Cl. ...................... 526/171; 526/127; 526/172; 502/155; 502/167
(58) Field of Search ................................. 526/127, 171, 526/172; 502/155, 167

(56) References Cited

U.S. PATENT DOCUMENTS 6,545,108 B1 * 4/2003 Moody et al. .............. 526/161

FOREIGN PATENT DOCUMENTS

| DE | 199 61 340 | 7/2001 |
|----|------------|--------|
| EP | 0 874 005 | 10/1998 |
| WO | 96/23010 | 8/1996 |
| WO | 98/27124 | 6/1998 |
| WO | 98 30609 | 7/1998 |
| WO | 98 42664 | 10/1998 |
| WO | 98/42665 | 10/1998 |
| WO | 00 50470 | 8/2000 |

OTHER PUBLICATIONS

A. Colautti et al.: "New coccidiostatic drugs of the 4–amino–4H–1,2,4–triazole series" Database CA 'Online? Chemical Abstracts Service, Columbus, Ohio, database accession No. 76:99572 XP002181151.

L.I. Kuznetsov et al.: "Azomethines of N–aminobenzazoles as novel ligand system" Database CA 'Online? Chemical Abstracts Service, Columbus, Ohio, database accession No. 97:16100 XP002181152.

P.V. Gilyanovskii et al.: "Luminescence and photochemistry of metal complexes with 4–salicyclideneamino–1,2,4–triazole" Database CA 'Online? Chemical Abstracts Service, Columbus, Ohio, database accession No. 103:133931 XP002181153.

A. Bach et al.: "Metal chelates of N–(1–pyrrolyl)salicycladimines and their structure determination by x–ray structure analysis and x–ray absorption spectroscopy (XANES)" Database CA 'Online? Chemical Abstracts Service, Columbus, Ohio, database accession No. 125:211201 XP002181154.

Changfeng Wang et al.: "Synthesis and properties of copper complexes of symmetrical triazole Schiff bases" Database CA 'Online? Chemcial Abstracts Service, Columbus, Ohio, database accession No. 127:184821 XP002181155.

Hans–Herbert Brintzinger et al.: "Stereospezifische olefinpolymerisation mit chialen metallocenkatalysaloren" Agnew Chem., vol. 107, pp. 1255–1283 1995.

Anke Held et al.: "Coordination polymerization of ethylene in water by Pd(II) and Ni(II) catalysts" J. Chem. Soc., Chem. Commun., pp. 301–302 2000.

* cited by examiner

*Primary Examiner*—Robert D. Harlan
(74) *Attorney, Agent, or Firm*—Oblon, Spivak, McClelland, Maier & Neustadt, P.C.

(57) ABSTRACT

Complexes of the formula I,

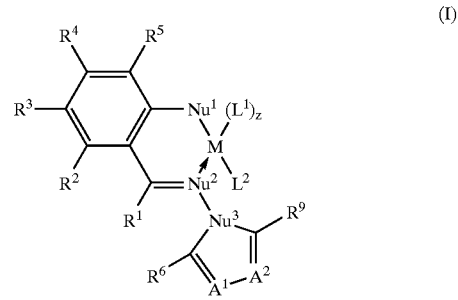

where M is an element of group 6 to 10 of the Period Table of the Elements, preferably Ni, can be used for the polymerization and copolymerization of olefins, for example in suspension polymerisation processes, gas-phase polymerization processes, bulk polymerization processes or emulsion polymerization processes.

20 Claims, No Drawings

LIGANDS, COMPLEX COMPOUNDS AND THEIR USE FOR POLYMERISING OLEFINS

BACKGROUND OF THE INVENTION

1. Field of the Invention

The present invention relates to complexes of the formula I,

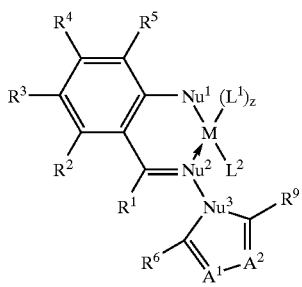

where the variables are defined as follows:
M is an element of groups 6 to 10 of the Periodic Table of the Elements,
$Nu^1$ is selected from among O, S and Se;
$Nu^2$, $Nu^3$ are selected from among N and P,
$A^1$ is N or C—$R^7$ or Si—$R^7$,
$A^2$ is N or C—$R^8$ or Si—$R^8$,
$R^1$ to $R^9$ are selected from among
  hydrogen,
  $C_1$–$C_8$-alkyl, substituted or unsubstituted,
  $C_2$–$C_8$-alkenyl, substituted or unsubstituted and having from one to 4 isolated or conjugated double bonds;
  $C_3$–$C_{12}$-cycloalkyl, substituted or unsubstituted,
  $C_7$–$C_{13}$-aralkyl,
  $C_6$–$C_{14}$-aryl, unsubstituted or monosubstituted or polysubstituted by identical or different substituents selected from among
    $C_1$–$C_8$-alkyl, substituted or unsubstituted,
    $C_3$–$C_{12}$-cycloalkyl,
    $C_7$–$C_{13}$-aralkyl,
    $C_6$–$C_{14}$-aryl,
    halogen,
    $C_1$–$C_6$-alkoxy, substituted or unsubstituted,
    $C_6$–$C_{14}$-aryloxy,
    $SiR^{10}R^{11}R^{12}$ and O—$SiR^{10}R^{11}R^{12}$;
  five- and six-membered nitrogen-containing heteroaryl radicals, unsubstituted or monosubstituted or polysubstituted by identical or different substituents selected from among
    $C_1$–$C_8$-alkyl, substituted or unsubstituted,
    $C_3$–$C_{12}$-cycloalkyl,
    $C_7$–$C_{13}$-aralkyl,
    $C_6$–$C_{14}$-aryl,
    halogen,
    $C_1$–$C_6$-alkoxy,
    $C_6$–$C_{14}$-aryloxy,
    $SiR^{10}R^{11}R^{12}$ and O—$SiR^{10}R^{11}R^{12}$;
where adjacent radicals $R^1$ to $R^9$ may be joined to one another to form a 5- to 12-membered ring;
$L^1$ is an uncharged organic or inorganic ligand,
$L^2$ is an organic or inorganic anionic ligand, where $L^1$ and $L^2$ may be joined to one another by one or more covalent bonds,
z is an integer from 1 to 3,
$R^{10}$ to $R^{12}$ are identical or different and are selected from among hydrogen, $C_1$–$C_8$-alkyl, $C_3$–$C_{12}$-cycloalkyl, $C_7$–$C_{13}$-aralkyl and $C_6$–$C_{14}$-aryl.

The present invention also relates to a process for preparing the complexes of the present invention from ligands of the formula II,

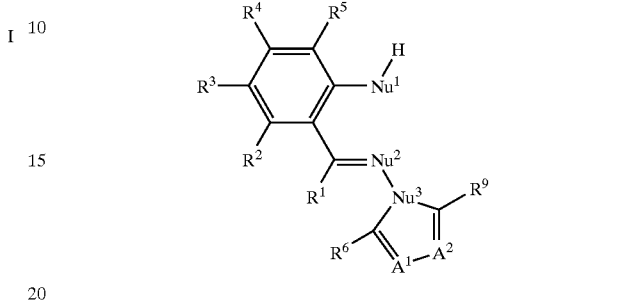

and to a process for preparing ligands of the formula II.

The present invention additionally relates to a process for preparing supported polymerization catalysts using a complex of the formula I and to a process for the polymerization or copolymerization of olefins using the supported catalysts of the present invention.

Finally, the present invention relates to a process for the emulsion polymerization and emulsion copolymerization of olefins using a complex of the formula IV.

2. Description of the Background

Polymers and copolymers of olefins are of great economic importance because the monomers are readily available in large quantities and because the polymers can be varied within a wide range by variation of the production process or the processing parameters. The catalyst used is of particular importance in the production process. Apart from Ziegler-Natta catalysts, there is increasing interest in single-site catalysts in which central atoms which have been examined in detail include not only Zr as, for example, in metallocene catalysts (H.-H. Brintzinger et al., Angew. Chem. 1995, 107, 1255) but also Ni or Pd (WO 96/23010) or Fe and Co (e.g. WO 98/27124). The complexes of Ni, Pd, Fe and Co are also referred to as complexes of late transition metals.

Metallocene catalysts have disadvantages for industrial use. The most frequently used metallocenes, i.e. zirconocenes and hafnocenes, are sensitive to hydrolysis. In addition, most metallocenes are sensitive to many catalyst poisons such as alcohols, ethers or CO, which makes careful purification of the monomers necessary.

While Ni or Pd complexes (WO 96/23010) catalyze the formation of highly branched polymers which are of little commercial interest, the use of Fe or Co complexes leads to the formation of highly linear polyethylene having very low proportions of comonomer.

Furthermore, complexes by means of which ethylene can be polymerized or copolymerized in the presence of water have been examined.

WO 98/42664 describes complexes of the formula A

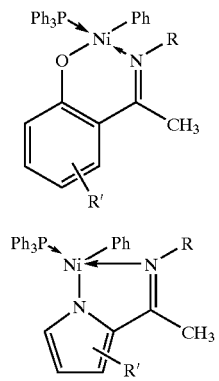

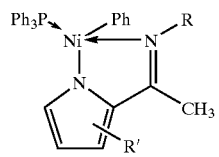

and closely related derivatives containing salicylaldimine ligands and their use for the polymerization of olefins.

WO 98/42665 describes complexes of the formula B and closely related derivatives and their use for the polymerization of olefins.

In the complexes of both the formulae A and B, the radical R on the imine nitrogen is a $C_1$–$C_{11}$-alkyl group or an ortho-substituted phenyl group. However, their activity is still in need of improvement.

It is also known that the complexes of the formulae A and B remain polymerization-active in the presence of small amounts of water, without the catalytic activity being adversely affected (WO 98/42664, in particular page 17, line 14 ff; WO 98/42665, p. 16, line 13). However, these amounts of water must not exceed 100 equivalents, based on the complex (WO 98/42664, page 17, lines 33–35; WO 98/42665, page 16, lines 30–31). Under these conditions, however, it is not possible to carry out an emulsion polymerization.

WO 98/30609 discloses derivatives of A which are suitable for the polymerization of ethylene and propylene. Their activity in this respect is not always satisfactory.

EP-A 0 874 005 discloses further polymerization-active complexes. These complexes are preferably titanium complexes containing salicylaldimine ligands. These too bear phenyl substituents or substituted phenyl substituents on the aldimine nitrogen (pages 18–23) or else the aldimine nitrogen is built into a 6-membered ring (pages 31–32). However, they have a high sensitivity to polar compounds such as water, alcohols or ethers.

In DE-A 199 61 340, published on . . . , it is shown that complexes of late transition metals of the formulae C and D

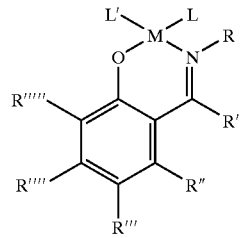

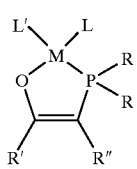

where R to R"'" are each hydrogen, alkyl, $C_7$–$C_{13}$-aralkyl or $C_6$–$C_{14}$-aryl, and mixtures thereof are suitable for polymerizing ethylene by emulsion polymerization. However, the activities are still in need of improvement. In A. Held et al., J. Chem. Soc., Chem. Commun. 2000, 301, it is shown that complexes of the formula C in which R is phenyl and R" is an $SO_3$— group are suitable for polymerizing ethylene in an aqueous medium. The activity of C is still not optimal.

Owing to the great commercial importance of polyolefins, the search for very versatile polymerization-active complexes having the highest possible activity continues to be of great importance.

SUMMARY OF THE INVENTION

Specific objects of the present invention are to provide novel complexes which are suitable for the polymerization of olefins;

to provide a process for preparing the polymerization-active complexes;

to provide a process for the polymerization or copolymerization of olefins using the polymerization-active complexes;

to provide supported catalysts for the polymerization of olefins and also a process for preparing the polymerization-active supported catalysts using the polymer-active complexes;

to polymerize and copolymerize olefins using the polymerization-active supported catalysts;

to provide a process for the emulsion polymerization or copolymerization of olefins, in particular ethylene, using the complexes of the present invention.

DETAILED DESCRIPTION OF THE PREFERRED EMBODIMENTS

We have found that these objects are achieved by means of complexes having the structures of the formula I defined at the outset.

In formula I, the variables are defined as follows:

M is an element of groups 6 to 10 of the Periodic Table of the Elements, preferably selected from among Cr, Fe, Pd and Ni, with particular preference being given to Ni;

$Nu^1$ is selected from among O, S and Se, with particular preference being given to oxygen;

$Nu^2$, $Nu^3$ are identical or different and are selected from among N or P, with particular preference being given to $Nu^2=Nu^3=$nitrogen;

$A^1$ is N or C—$R^7$ or Si—$R^7$, preferably N or C—$R^7$, particularly preferably C—$R^7$;

$A^2$ is N or C—$R^8$ or Si—$R^8$, preferably N or C—$R^8$, particularly preferably C—$R^8$;

$R^1$ to $R^9$ are identical or different and are selected from among hydrogen, $C_1$–$C_8$-alkyl groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_8$-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_2$–$C_8$-alkenyl having from one to 4 isolated or conjugated double bonds, for example vinyl, 1-allyl, 3-allyl, ω-butenyl, ω-pentenyl, ω-hexenyl, 1-cis-buta-1,3-dienyl and 1-cis-hexa-1,5-dienyl;

examples of substituted $C_2$–$C_8$-alkenyl groups are: isopropenyl, 1-isoprenyl, α-styryl, β-styryl, 1-cis-1,2-phenylethenyl and 1-trans-1,2-phenylethenyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

examples of substituted cycloalkyl groups are: 2-methylcyclopentyl, 3-methylcyclopentyl, cis-2,4-dimethylcyclopentyl, trans-2,4-dimethylcyclopentyl, cis-2,5-dimethylcyclopentyl, trans-2,5-dimethylcyclopentyl, 2,2,5,5-tetramethylcyclopentyl, 2-methylcyclohexyl, 3-methylcyclohexyl, 4-methylcyclohexyl, cis-2,6-dimethylcyclohexyl, trans-2,6-dimethylcyclohexyl, cis-2,6-diisopropylcyclohexyl, trans-2,6-diisopropylcyclohexyl, 2,2,6,6-tetramethylcyclohexyl, 2-methoxycyclopentyl, 2-methoxycyclohexyl, 3-methoxycyclopentyl, 3-methoxycyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,6,6-tetrachlorocyclohexyl, 2-thiomethylcyclopentyl, 2-thiomethylcyclohexyl, 3-thiomethylcyclopentyl, 3-thiomethylcyclohexyl and further derivatives;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

$C_6$–$C_{14}$-aryl such as phenyl, 1-naphthyl, 2-naphthyl, 1-anthryl, 2-anthryl, 9-anthryl, 1-phenanthryl, 2-phenanthryl,3-phenanthryl, 4-phenanthryl and 9-phenanthryl substituted by one or more identical or different substituents selected from among $C_1$–$C_8$-alkyl groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_8$-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

halogen, for example fluorine, chlorine, bromine and iodine, particularly preferably fluorine and chlorine;

$C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

$C_6$–$C_{14}$-aryloxy groups such as phenoxy, ortho-cresyloxy, meta-cresyloxy, para-cresyloxy, α-naphthoxy, β-naphthoxy and 9-anthryloxy;

silyl groups $SiR^{10}R^{11}R^{12}$, where $R^{10}$ to $R^{12}$ are selected independently from among hydrogen, $C_1$–$C_8$-alkyl groups, the benzyl radical and $C_6$–$C_{14}$-aryl groups; preference is given to the trimethylsilyl, triethylsilyl, triisopropylsilyl, diethylisopropylsilyl, dimethylhexylsilyl, tert-butyldimethylsilyl, tert-butyldiphenylsilyl, tribenzylsilyl, triphenylsilyl and tri-para-xylylsilyl groups; particular preference is given to the trimethylsilyl group and the tert-butyldimethylsilyl group;

silyloxy groups $OSiR^{10}R^{11}R^{12}$, where $R^{10}$ to $R^{12}$ are selected independently from among hydrogen, $C_1$–$C_8$-alkyl groups, the benzyl radical and $C_6$–$C_{14}$-aryl groups; preference is given to the trimethylsilyloxy, triethylsilyloxy, triisopropylsilyloxy, diethylisopropylsilyloxy, dimethylhexylsilyloxy, tert-butyldimethylsilyloxy, tert-butyldiphenylsilyloxy, tribenzylsilyloxy, triphenylsilyloxy and tri-para-xylylsilyloxy groups; particular preference is given to the trimethylsilyloxy group and the tert-butyldimethylsilyloxy group;

five- and six-membered nitrogen-containing heteroaryl radicals such as N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl;

five- and six-membered nitrogen-containing heteroaryl radicals such as N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl substituted by one or more identical or different substituents selected from among $C_1$–$C_8$-alkyl groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_8$-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

halogen, for example fluorine, chlorine, bromine and iodine, particularly preferably fluorine and chlorine;

$C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

$C_6$–$C_{14}$-aryloxy groups such as phenoxy, ortho-cresyloxy, meta-cresyloxy, para-cresyloxy, α-naphthoxy, β-naphthoxy and 9-anthryloxy;

silyl groups $SiR^{10}R^{11}R^{12}$, where $R^{10}$ to $R^{12}$ are selected independently from among hydrogen, $C_1$–$C_8$-alkyl groups, the benzyl radical and $C_6$–$C_{14}$-aryl groups; preference is given to the trimethylsilyl, triethylsilyl, triisopropylsilyl, diethylisopropylsilyl, dimethylhexylsilyl, tert-butyldimethylsilyl, tert-butyldiphenylsilyl, tribenzylsilyl, triphenylsilyl and tri-para-xylylsilyl groups; particular preference is given to the trimethylsilyl group and the tert-butyldimethylsilyl group;

silyloxy groups $OSiR^{10}R^{11}R^{12}$, where $R^{10}$ to $R^{12}$ are selected independently from among hydrogen, $C_1$–$C_8$-alkyl groups, the benzyl radical and $C_6$–$C_{14}$-aryl groups; preference is given to the trimethylsilyloxy, triethylsilyloxy, triisopropylsilyloxy, diethylisopropylsilyloxy, dimethylhexylsilyloxy, tert-butyldimethylsilyloxy, tert-butyldiphenylsilyloxy, tribenzylsilyloxy, triphenylsilyloxy and tri-para-xylylsilyloxy groups; particular preference is given to the trimethylsilyloxy group and the tert-butyldimethylsilyloxy group.

In a particularly preferred embodiment, $R^1$, $R^2$ and $R^4$ are each hydrogen. In a likewise particularly preferred embodiment, $R^6$ and $R^9$ are $C_1$–$C_8$-alkyl, branched or unbranched. $R^3$ and $R^5$ are particularly preferably, independently of one another, hydrogen or $C_1$–$C_8$-alkyl, branched or unbranched.

In a particular embodiment, adjacent radicals $R^1$ to $R^9$ may be joined to one another to form a 5- to 12-membered ring. For example, $R^6$ and $R^7$ may together be: —$(CH_2)_3$— (trimethylene), —$(CH_2)_4$— (tetramethylene), —$(CH_2)_5$— (pentamethylene), —$(CH_2)_6$— (hexamethylene), —$CH_2$—CH=CH—, —$CH_2$—CH=CH—$CH_2$—, —CH=CH—CH=CH—, —O—$CH_2$—O—, —O—CHMe-O—, —O—CH—$(C_6H_5)$—O—, —O—$CH_2$—$CH_2$—O—, —O—$CMe_2$-O—, —NMe-$CH_2$—$CH_2$—NMe-, —NMe-$CH_2$—NMe- or —O—$SiMe_2$—O— where Me=$CH_3$. In a preferred example, $R^6$ and $R^7$ together form a 1,3-butadiene-1,4-diyl unit which may in turn bear one or more $C_1$–$C_8$-alkyl substituents. In a further preferred example, $R^6$ and $R^7$ and also $R^8$ and $R^9$, in each case pairwise, together form a 1,3-butadiene-1,4-diyl unit which may in turn bear one or more $C_1$–$C_8$-alkyl substituents.

$L^1$ is selected from among uncharged inorganic and organic ligands, for example from among phosphines of the formula $(R^{13})_xPH_{3-x}$ or amines of the formula $(R^{13})_xNH_{3-x}$, where x is an integer from 0 to 3. However, ethers $(R^{13})_2O$ such as dialkyl ethers, e.g. diethyl ether, or cyclic ethers, for example tetrahydrofuran, $H_2O$, alcohols $(R^{13})OH$ such as methanol or ethanol, pyridine, pyridine derivatives of the formula $C_5H_{5-x}(R^{13})_xN$, for example 2-picoline, 3-picoline, 4-picoline, 2,3-lutidine, 2,4-lutidine, 2,5-lutidine, 2,6-lutidine or 3,5-lutidine, CO, $C_1$–$C_{12}$-alkyl nitriles or $C_6$–$C_{14}$-aryl nitriles, e.g. acetonitrile, propionitrile, butyronitrile or benzonitrile, are also suitable. It is also possible to use singly or multiply ethylenically unsaturated double bond systems such as ethenyl, propenyl, cis-2-butenyl, trans-2-butenyl, cyclohexenyl or norbornenyl, as ligand.

$L^2$ is selected from among inorganic and organic anionic ligands, for example from among halide ions such as fluoride, chloride, bromide and iodide, preferably chloride and bromide, amide anions $(R^{13})_{x-1}NH_{2-x}$, where x is an integer from 0 to 3, $C_1$–$C_6$-alkyl anions such as $(CH_3)^-$, $(C_2H_5)^-$, $(C_3H_7)^-$, $(n-C_4H_9)^-$, $(tert-C_4H_9)^-$ or $(C_6H_{14})^-$;

allyl anions or methallyl anions, benzyl anions and
aryl anions such as $(C_6H_5)^-$.

z is an integer from 1 to 3, for example 0, 1, 2 or 3.

$R^{13}$ are identical or different and are selected from among
hydrogen,
$C_1-C_8$-alkyl groups,
the benzyl radical and
$C_6-C_{14}$-aryl groups, where these groups are as defined above and two radicals $R^{13}$ may be covalently bound to one another.

In a preferred embodiment, $L^1$ and $L^2$ are joined to one another by one or more covalent bonds. Examples of such ligands are 1,5-cyclooctadienyl ligands ("COD"), 1,6-cyclodecenyl ligands and 1,5,9-all-trans-cyclododecatrienyl ligands.

In a further preferred embodiment, $L^1$ is tetramethylethylenediamine, in which case only one nitrogen coordinates to the nickel.

The novel complexes of the formula I are generally prepared from ligands of the formula II in which the variables are as defined above. To synthesize the complexes of the present invention, the ligands are firstly deprotonated by means of a base and subsequently reacted with metal compounds of the formulae $MX_2$, $MX_3$, $MX_4$ or $ML^1L^2$.

As base, it is possible to use the metal alkyls customary in organometallic chemistry, for example methyllithium, ethyllithium, n-butyllithium, sec-butyllithium, tert-butyllithium or hexyllithium, also Grignard compounds such as ethylmagnesium bromide, also lithium amide, sodium amide, potassium amide, potassium hydride or lithium diisopropylamide ("LDA"). Solvents which have been found to be useful are high-boiling solvents such as toluene, ortho-xylene, meta.-xylene, para-xylene, ethylbenzene or mixtures thereof, also noncyclic or cyclic ethers such as 1,2-dimethoxyethane, tetrahydrofuran or diethyl ether.

This deprotonation is generally complete after a few hours; reaction times of from 2 to 10 hours are useful and preference is given to from 3 to 5 hours. The temperature conditions are generally not critical; carrying out the reaction at from −90° C. to −20° C. has been found to be advantageous.

The deprotonated ligand and the metal compound of the formula $MX_2$, $MX_3$, $MX_4$ or $ML^1L^2$ are subsequently reacted with one another.

X are identical or different and are selected from among:
halogen such as fluorine, chlorine,.bromine and iodine, preferably chlorine and bromine;
$C_1-C_8$-alkyl groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1-C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1-C_4$-alkyl such as methyl, ethyl, n-propyl, isopropyl, n-butyl, isobutyl, sec-butyl and tert-butyl;
$C_3-C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;
$C_7-C_{13}$-aralkyl, preferably $C_7-C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;
$C_6-Cl_4$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

X are preferably identical.

$MX_2$, $MX_3$, $MX_4$ or $ML^1L^2$ may, if desired, be stabilized by uncharged ligands. Suitable uncharged ligands are the customary ligands of coordination chemistry, for example cyclic and noncyclic ethers, amines, diamines, nitriles, isonitriles or phosphines. Particular preference is given to diethyl ether, tetrahydrofuran, 1,2-dimethoxyethane, tetramethylethylenediamine, acetonitrile or triphenylphosphine. Especially in cases in which, for example, nickel dialkyl compounds are to be used, uncharged ligands have been found to be useful. The uncharged ligands can also be used as solvent.

The conditions for the reaction are not critical per se; it is usual to mix the deprotonated ligand II and $MX_2$ or $MX_4$ with one another in a suitable solvent such as benzene, toluene, ethylbenzene, ortho-xylene, meta-xylene or para-xylene, chlorobenzene, cyclohexane, acetonitrile, tetrahydrofuran, methylene chloride or mixtures thereof. Suitable reaction temperatures are in the range from −100° C. to +150° C., preferably from −78° C. to +100° C. It is important that the reaction is carried out in the absence of oxygen and moisture.

Suitable molar ratios of ligand to M are in the range from 5:1 to 1:5. Since, however, the novel ligands of the formula II are the more difficult-to-obtain reactants, molar ratios of ligand:M in the range from 1:1 to 1:3 are preferred; particular preference is given to stoichiometric amounts.

The novel complexes of the formula I are purified by methods customary in organometallic chemistry, with crystallization being particularly preferred. Filtration through filter aids such as Celite® is also useful.

It is not necessary in all cases to isolate the complexes of the present invention in order to carry out the polymerization. It is also possible to react a ligand of the formula II with a suitable metal compound of the formula $MX_2$, $MX_3$, $MX_4$ or $ML^1L^2$ only just before the polymerization and thus generate the complexes in situ.

If X in the metal compound of the formula $MX_2$, $MX_3$ or $MX_4$ or $L^2$ in $ML^1L^2$ is selected from the group consisting of $C_1-C_6$-alkyl groups, benzyl anions or aryl anions, the deprotonation of the ligand of the formula II can be dispensed with. In this case, it has been found to be preferable not to isolate the complexes of the present invention but instead to generate them in situ only immediately prior to the polymerization.

The novel ligands of the formula II are prepared by condensation of a carbonyl compound of the formula III

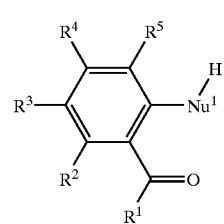

III with a compound of the formula IV,

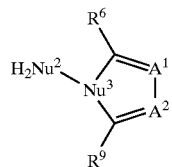

where the variables are as defined at the outset.

The synthesis of the ligands of the formula II is carried out at from −78° C. to +150° C., preferably from −10° C. to +75° C. As catalyst, a Lewis acid or a Brønsted acid is added. Lewis acids which have been found to be particularly effective are aluminum alkyls such as Al(CH$_3$)$_3$, Al(C$_2$H$_5$)$_3$ or BF$_3$. Brønsted acids which can be used are, for example, sulfuric acid, phosphoric acid, HF, toluenesulfonic acid or amidosulfonic acid. The reaction time is from 1 to 48 hours, preferably from 12 to 24 hours. Aprotic media, in particular toluene and benzene, have been found to be preferred as solvents when aluminum alkyls or BF$_3$ are used as catalysts; otherwise alcohols such as methanol, ethanol or mixtures thereof can also be used. It has been found to be useful, particularly when using a Brønsted acid as catalyst, to remove the water formed by azeotropic distillation with the aid of a water separator.

Compounds of the formula III and a method of preparing them are described in WO 98/42664.

The synthesis of the compounds of the formula IV can be carried out by the method described in DE-A 199 44 993, published on . . . , by firstly reacting a suitable 1,4-dicarbonyl compound of the formula V

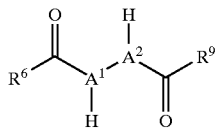

with one equivalent of acetylhydrazine or benzoylhydrazine in the presence of a catalytic amount of acid, preferably para-toluenesulfonic acid, in an inert solvent, preferably toluene, to form an N-acetyl- or N-benzoyl-protected derivative of IV and subsequently saponifying this with an excess of base, preferably KOH, in a high-boiling organic solvent such as ethylene glycol.

For the novel complexes of the formula I to be catalytically active, they have to be activated. Suitable activators are selected aluminum or boron compounds having electron-withdrawing groups (e.g. trispentafluorophenylborane, trispentafluorophenylaluminum, N,N-dimethylanilinium tetrakispentafluorophenylborate, tri-n-butylammonium tetrakispentafluorophenylborate, N,N-dimethylanilinium tetrakis(3,5-bisperfluoromethyl)phenylborate, tri-n-butylammonium tetrakis(3,5-bisperfluoromethyl)phenylborate and tritylium tetrakispentafluorophenylborate). Preference is given to dimethylanilinium tetrakispentafluorophenylborate, tritylium tetrakispentafluorophenylborate and trispentafluorophenylborane.

If boron or aluminum compounds are used as activators for the novel complexes of the formula I, they are generally used in a molar ratio to M of from 1:10 to 10:1, preferably from 1:2 to 5:1 and particularly preferably from 1:1.5 to 1.5:1.

Another class of suitable activators is formed by aluminoxanes.

The structure of aluminoxanes is not known precisely. They are products obtained by careful partial hydrolysis of aluminum alkyls (cf. DE-A 30 07 725). These products are not present as pure compounds, but rather as mixtures of open-chain and cyclic structures of types VI a and VI b. The compounds in these mixtures are presumably in dynamic equilibrium with one another.

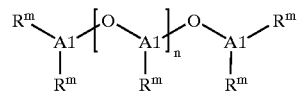

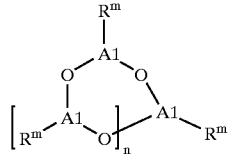

In formulae VI a and VI b, the radicals R$'''$ are, independently of one another, C$_1$–C$_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl or n-dodecyl; preferably C$_1$–C$_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably methyl;

C$_3$–C$_{12}$-cycloalkyl such as cyclopropyl, cyclobutyl, cyclopentyl, cyclohexyl, cycloheptyl, cyclooctyl, cyclononyl, cyclodecyl, cycloundecyl or cyclododecyl; preferably cyclopentyl, cyclohexyl or cycloheptyl;

C$_7$–C$_{20}$-aralkyl, preferably C$_7$–C$_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl or 4-phenylbutyl, particularly preferably benzyl, or C$_6$–C$_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl or 9-phenanthryl, preferably phenyl, 1-naphthyl and 2-naphthyl, particularly preferably phenyl; and n is an integer from 0 to 40, preferably from 1 to 25 and particularly preferably from 2 to 22.

Cage-like structures for aluminoxanes have also been discussed in the literature (Y. Koide, S. G. Bott, A. R. Barron Organometallics 1996, 15, 2213–26; A. R. Barron Macromol. Symp. 1995, 97, 15–25). Regardless of the actual structure of aluminoxanes, they are suitable as activators for the novel metal complexes of the formula I.

Mixtures of various aluminoxanes are particularly preferred activators in those cases in which the polymerization is carried out in a solution in a paraffin, for example n-heptane or isododecane. A particularly preferred mixture is the commercial product CoMAO of the formula [(CH$_3$)$_{0.9}$(iso-C$_4$H$_9$)$_{0.1}$AlO]$_n$ obtainable from Witco GmbH.

To activate the novel complexes of the formula I by means of aluminoxanes, an excess of aluminoxane, based on M, is generally necesssary. Appropriate molar ratios M:Al are in the range from 1:10 to 1:10 000, particularly preferably from 1:50 to 1:1 000 and particularly preferably from 1:100 to 1:500.

According to prevailing opinion, activators for metal complexes of the formula I abstract a ligand $L^1$ or $L^2$. Rather than aluminum alkyl compounds of the formulae VI a and VI b or the above-described aluminum or boron compounds having electron-withdrawing groups, the activator can comprise, for example, olefin complexes of rhodium or nickel.

Preferred nickel(olefin)$_y$ complexes, where y=1, 2, 3 or 4, which are commercially available from Aldrich are Ni(C$_2$H$_4$)$_3$, Ni(1,5-cyclooctadiene)$_2$ "Ni(COD)$_2$", Ni(1,6-cyclodecadiene)$_2$ or Ni(1,5,9-all-trans-cyclododecatriene)$_2$. Particular preference is given to Ni(COD)$_2$.

Particularly useful activators of this type are mixed ethylene/1,3-dicarbonyl complexes of rhodium, for example rhodium(ethylene) acetylacetonate Rh(acac)(CH$_2$=CH$_2$)$_2$, rhodium(ethylene) benzoylacetonate Rh(C$_6$H$_5$—CO—CH—CO—CH$_3$)(CH$_2$=CH$_2$)$_2$ or Rh(C$_6$H$_5$—CO—CH—CO—C$_6$H$_5$)(CH$_2$=CH$_2$)$_2$. Most suitable is Rh(acac)(CH$_2$=CH$_2$)$_2$. This compound can be synthesized by the method described by R. Cramer in Inorg. Synth. 1974, 15, 14.

Some complexes of the formula I can be activated by means of ethylene. The ease of the activation reaction depends critically on the nature of the ligand $L^1$.

The chosen complex of the formula I and the activator together form a catalyst system.

The activity of the catalyst system of the present invention can be increased by addition of further aluminum alkyl of the formula Al(R'''')$_3$ or aluminoxanes, particularly when compounds of the formula VI a or VI b or the abovementioned aluminum or boron compounds having electron-withdrawing groups are used as activators; aluminum alkyls of the formula Al(R'''')$_3$ or aluminoxanes can also act as molar mass regulators. A further effective molar mass regulator is hydrogen. The molar mass can be particularly effectively regulated by means of the reaction temperature and the pressure. If the use of a boron compound as described above is desired, the addition of an aluminum alkyl of the formula Al(R'''')$_3$ is particularly preferred.

It has been found that the novel complexes of the formula I are suitable for polymerizing olefins. They particularly readily polymerize and copolymerize ethylene and propylene.

Pressure and temperature conditions during the polymerization can be chosen within wide limits. A pressure range from 0.5 bar to 4000 bar has been found to be useful; preference is given to from 10 to 75 bar or high-pressure conditions of from 500 to 2500 bar. A temperature range from 0 to 120° C. has been found to be useful; preference is given to from 40 to 100° C. and particular preference is given to from 50 to 85° C.

Examples of monomers are the following olefins: ethylene, propylene, 1-butene, 1-pentene, 1-hexene, 1-octene, 1-decene and 1-undecene, with preference being given to propylene and ethylene and particular preference being given to ethylene.

Suitable comonomers are α-olefins such as from 0.1 to 20 mol % of 1-butene, 1-pentene, 1-hexene, 4-methyl-1-pentene, 1-octene, 1-decene or 1-undecene. Further suitable comonomers are isobutene and styrene, also internal olefins such as cyclopentene, cyclohexene, norbornene and norbornadiene.

Solvents which have found to be useful are toluene, ortho-xylene, meta-xylene, para-xylene or ethylbenzene and mixtures thereof, also diethyl ether, tetrahydrofuran, chlorobenzene, 1,3-dichlorobenzene, dichloromethane and, under high-pressure conditions, supercritical ethylene.

The novel complexes of the formula I can be regulated by means of hydrogen in the polymerization, i.e. the molecular weight of the polymers obtainable by means of the catalyst system of the present invention can be reduced by addition of hydrogen. If sufficient hydrogen is added, waxes are obtained, with the hydrogen concentration required depending, inter alia, on the type of polymerization plant used.

For the novel complexes of the formula I to be able to be used in modern polymerization processes such as suspension processes, bulk polymerization processes or gas-phase processes, it is necessary for them to be immobilized on a solid support. Otherwise, polymer morphology problems (lumps, deposits on walls, blockages in lines or heat exchangers) can occur and force shutdown of the plant. Such an immobilized complex of the formula I is referred to as catalyst.

It has been found that the novel complexes of the formula I can be readily deposited on a solid support. Possible support materials are, for example, porous metal oxides of metals of groups 2 to 14 or mixtures thereof, also sheet silicates and zeolites. Preferred examples of metal oxides of groups 2 to 14 are SiO$_2$, B$_2$O$_3$, Al$_2$O$_3$, MgO, CaO and ZnO. Preferred sheet silicates are montmorillonites and bentonites; as zeolite, preference is given to using MCM-41.

Particularly preferred support materials are spherical silica gels and aluminosilicate gels of the formula SiO$_2$.a Al$_2$O$_3$, where a is generally in the range from 0 to 2, preferably from 0 to 0.5. Such silica gels are commercially available, e.g. Silica Gel SG 332, Sylopol® 948 or 952 or S 2101 from W. R. Grace or ES 70X from Crosfield.

As regards the particle size of the support material, mean particle diameters of from 1 to 300 μm, preferably from 20 to 80 μm, have been found to be useful. This particle diameter is determined by known methods such as sieve methods. The pore volume of these supports is from 1.0 to 3.0 ml/g, preferably from 1.6 to 2.2 ml/g and particularly preferably from 1.7 to 1.9 ml/g. The BET surface area is from 200 to 750 m$^2$/g, preferably from 250 to 400 m$^2$/g.

To remove adhering impurities, in particular moisture, from the support material, the support materials can be baked at, for example, from 45 to 1000° C. before doping. Temperatures of from 100 to 750° C. are particularly useful for silica gels and other metal oxides. This baking can be carried out for a period of from 0.5 to 24 hours, preferably from 1 to 12 hours. The pressure conditions depend on the method chosen; baking can be carried out in a fixed-bed process, a stirred vessel or else in a fluidized-bed process. Baking can quite generally be carried out at atmospheric pressure. However, it is advantageous to employ reduced pressures of from 0.1 to 500 mbar, particularly advantageously from 1 to 100 mbar and very particularly advantageously from 2 to 20 mbar. In fluidized-bed processes, on the other hand, it is advisable to employ slightly superatmospheric pressure in the range from 1.01 bar to 5 bar, preferably from 1.1 to 1.5 bar.

Chemical pretreatment of the support material with an alkyl compound such as an aluminum alkyl, a lithium alkyl or an aluminoxane is likewise possible.

For polymerization by the suspension method, use is made of suspension media in which the desired polymer is insoluble or only slightly soluble, because otherwise deposits of product occur in parts of the plant in which the product is separated off from the suspension medium and force repeated shutdowns and cleaning operations. Suitable suspension media are saturated hydrocarbons such as propane, n-butane, isobutane, n-pentane, isopentane, n-hexane, isohexane and cyclohexane, with preference being given to isobutane.

Pressure and temperature conditions during the polymerization can be chosen within wide limits. A suitable pressure range has been found to be from 0.5 bar to 150 bar, preferably from 10 to 75 bar. A suitable temperature range has been found to be from 0 to 120° C., preferably from 40 to 100° C.

Examples of monomers are the following olefins: ethylene, propylene, 1-butene, 1-pentene, 1-hexene, 1-octene, 1-decene and 1-undecene, with preference being given to ethylene.

Suitable comonomers are a-olefins such as from 0.1 to 20 mol % of 1-butene, 1-pentene, 1-hexene, 4-methyl-1-pentene, 1-octene, 1-decene or 1-undecene. Further suitable comonomers are isobutene and styrene, also internal olefins such as cyclopentene, cyclohexene, norbornene and norbornadiene.

The novel catalysts can also be regulated by means of hydrogen, i.e. the molecular weight of the polymers obtainable by means of the catalysts of the present invention can be reduced by addition of hydrogen. If sufficient hydrogen is added, waxes are obtained, with the hydrogen concentration required depending, inter alia, on the type of polymerization plant used. Addition of hydrogen increases the activity of the catalysts of the present invention.

The catalysts of the present invention can also be used together with one or more other polymerization catalysts known per se. Thus, they can be used together with Ziegler-Natta catalysts, supported metallocene catalysts of transition metals of groups 4 to 6 of the Periodic Table of the Elements, catalysts comprising late transition metals (WO 96/23010), Fe or Co complexes with pyridyldiimine ligands as disclosed in WO 98/27124, or chromium oxide catalysts of the Phillips type.

It is possible, on the one hand, to mix various catalysts with one another and meter them into the reactor together or to use cosupported complexes on a common support or else to meter various catalysts into the polymerization vessel separately at the same point or at different points.

Furthermore, it has been found that the novel complexes of the formula I, in particular those in which M=Ni, are particularly suitable for the polymerization or copolymerization of 1-olefins, preferably ethylene, in emulsion polymerization processes.

Apart from other 1-olefins as comonomers, for example propene, 1-butene, 1-hexene, 1-octene or 1-decene, polar comonomers can also be incorporated by means of the catalyst system of the present invention. It is possible to use from 0.1 to 50 mol % of comonomer. Preference is given to acrylates such as acrylic acid, methyl acrylate, ethyl acrylate, 2-ethylhexyl acrylate, n-butyl acrylate or tert-butyl acrylate;

methacrylic acid, methyl methacrylate, ethyl methacrylate, n-butyl methacrylate or tert-butyl methacrylate;

vinyl carboxylates, particularly preferably vinyl acetate, unsaturated dicarboxylic acids, particularly preferably maleic acid, unsaturated dicarboxylic acid derivatives, particularly preferably maleic anhydride and alkylimides of maleic acid, for example N-methylmaleimide.

It is also possible to prepare terpolymers comprising at least 2 of the abovementioned monomers plus ethylene.

The emulsion polymerization of the 1-olefins using the novel metal complexes of the formula I can be carried out in a manner known per se.

Here, the order of addition of the reagents in the polymerization is not critical. Thus, it is possible firstly to inject gaseous monomer into the reactor over the solvent or to meter in liquid monomer and subsequently to add the catalyst system. However, the solution of the catalyst system can also firstly be diluted with further solvent and monomer can subsequently be added.

The actual polymerization is usually carried out at a minimum pressure of 1 bar; below this pressure, the polymerization rate is too low. Preference is given to 2 bar and particular preference is given to a minimum pressure of 10 bar.

The maximum pressure is effectively 4000 bar; at higher pressures, the demands placed on the material of construction of the polymerization reactor are very high and the process becomes uneconomical. Preference is given to 100 bar and particular preference is given to 50 bar.

The polymerization temperature can be varied within a wide range. The minimum temperature is effectively 10° C., since the polymerization rate decreases at low temperatures. Preference is given to a minimum temperature of 40° C., particularly preferably 65° C. The maximum sensible temperature is 350° C., preferably 150° C., particularly preferably 100° C.

Before the polymerization, the complex of the formula I is dissolved in an organic solvent or in water. The solution is stirred or shaken for a number of minutes to ensure that it is clear. The stirring time can be, depending on the solubility of the structure concerned, from 1 to 100 minutes.

At the same time, any activator required is dissolved in a second portion of the same solvent or in acetone.

Suitable organic solvents are aromatic solvents such as benzene, toluene, ethylbenzene, ortho-xylene, meta-xylene and para-xylene and mixtures thereof. Further suitable solvents are cyclic ethers such as tetrahydrofuran and dioxane or noncyclic ethers such as diethyl ether, di-n-butyl ether, diisopropyl ether or 1,2-dimethoxyethane. It is also possible to use ketones such as acetone, methyl ethyl ketone or diisobutyl ketone, likewise amides such as dimethylformamide or dimethylacetamide. Mixtures of these solvents with one another or with water or alcohols such as methanol or ethanol are also useful.

Preference is given to acetone and water and to mixtures of acetone and water in any mixing ratio. The amount of solvent is likewise not critical, but it has to be ensured that the complex and the activator can be completely dissolved, otherwise losses in activity have to be expected. The dissolution process can, if desired, be accelerated by ultrasound treatment.

An emulsifier may be added if desired and can be dissolved in a third portion of the solvent or else together with the complex.

The amount of emulsifier is selected so that the mass ratio of monomer to emulsifier is greater than 1, preferably greater than 10 and particularly preferably greater than 20. The less emulsifier used, the better. The activity in the polymerization is significantly increased if an emulsifier is added. This emulsifier can be nonionic or ionic in nature.

Nonionic emulsifiers which can be used are, for example, ethoxylated monoalkylphenols, dialkylphenols and trialkylphenols (number of EO units: from 3 to 50, alkyl radical: $C_4$–$C_{12}$) and also ethoxylated fatty alcohols (number of EO units: from 3 to 80; alkyl radical: $C_8$–$C_{36}$). Examples of such emulsifiers are the Lutensol® grades from BASF AG or the Triton® grades from Union Carbide.

Customary anionic emulsifiers are, for example, alkali metal and ammonium salts of alkyl sulfates (alkyl radical:

$C_8$ to $C_{12}$), of sulfuric monoesters of ethoxylated alkanols (number of EO units: from 4 to 30, alkyl radical: $C_{12}$–$C_{18}$) and ethoxylated alkylphenols (number of EO units: from 3 to 50, alkyl radical: $C_4$–$C_{12}$), of alkylsulfonic acids (alkyl radical: $C_{12}$–$C_{18}$) and of alkylarylsulfonic acids (alkyl radical: $C_9$–$C_{18}$).

Suitable cationic emulsifiers are generally primary, secondary, tertiary or quaternary ammonium salts, alkanolammonium salts, pyridinium salts, imidazolinium salts, oxazolinium salts, orpholinium salts, thiazolinium salts and salts of amine oxides, quinolinium salts, isoquinolinium salts, tropylium salts, sulfonium salts and phosphonium salts bearing a $C_6$–$C_{18}$-alkyl, -aralkyl or heterocyclic radical. Examples which may be mentioned are dodecylammonium acetate or the corresponding hydrochloride, he chlorides or acetates of the various 2-(N,N,N-trimethylammonium) ethylparaffinic esters, N-cetylpyridinium chloride, N-laurylpyridinium sulfate and also N-cetyl-N,N,N-trimethylammonium bromide, N-dodecyl-N,N,N-trimethylammonium bromide, N,N-distearyl-N,N-dimethylammonium chloride and the Gemini surfactant N,N'-(lauryldimethyl)ethylenediamine dibromide. Numerous further examples may be found in H. Stache, Tensid-Taschenbuch, Carl-Hanser-Verlag, Munich, Vienna, 1981, and in McCutcheon's, Emulsifiers & Detergents, MC Publishing Company, Glen Rock, 1989.

The components, viz. complex in solution, if desired the solution of an emulsifier and if desired the solution of an activator, are subsequently introduced into the polymerization reactor. Polymerization reactors which have been found to be useful are stirred vessels and autoclaves and also tube reactors, with the tube reactors being able to be configured as loop reactors.

The monomer or monomers to be polymerized are mixed in the polymerization medium. The polymerization medium used can be water or a mixture of water with one or more of the abovementioned solvents. It should be ensured that the proportion of water is at least 50% by volume, preferably at least 90% by volume and particularly preferably at least 95% by volume, based on the total mixture.

The solutions of the complex, if desired of the activator and if desired of the emulsifier are combined with the mixture of monomer and aqueous polymerization medium. The order of addition of the various components is not critical per se. However, it is necessary that the components be combined sufficiently quickly for no crystallization of any sparingly soluble complexes formed as intermediates to occur.

The process of the present invention gives polyolefins and olefin copolymers in high yields, i.e. the activity of the complexes of the present invention is very high under the conditions of emulsion polymerization.

As polymerization processes, it is possible to use continuous and batchwise processes. Preference is given to semicontinuous (semibatch) processes in which, after mixing all components, further monomer or monomer mixtures are metered in during the course of the polymerization.

The process of the present invention initially gives aqueous polymer dispersions.

The mean particle diameters of the polymer particles in the dispersions produced according to the present invention are from 10 to 1000 nm, preferably from 50 to 500 nm and particularly preferably from 70 to 350 nm. The distribution of the particle diameters can be, but does not necessarily have to be, very narrow. For some applications, particularly those in which the solids contents are high (>55%), broad or bimodal distributions are even preferred.

The polymers obtained by the process of the present invention have industrially interesting properties. In the case of polyethylene, they have a high degree of crystallinity which can be confirmed, for example, by the number of branches. Less than 100 branches, preferably less than 50 branches, per 1000 carbon atoms of the polymer are found by $^1$H-NMR and $^{13}$C-NMR spectroscopy.

The melting enthalpies of the polyethylenes obtainable by means of the process of the present invention are greater than 100 J/g, preferably greater than 140 and particularly preferably greater than 180 J/g, measured by DSC.

The molecular weight distributions of the polyethylenes obtainable by means of the process of the present invention are narrow, i.e. the Q values are in the range from 1.1 to 3.5, preferably from 1.5 to 3.1.

Advantages of the dispersions obtained according to the present invention are, firstly, their low price due to the cheap monomers and process, and, secondly, that they are more stable to weathering than dispersions of polybutadiene or butadiene copolymers. Compared to dispersions of polymers comprising acrylates or methacrylates as main monomer, their lower tendency to undergo saponification is an advantage. A further advantage is that most olefins are volatile and residual unpolymerized monomers can easily be removed. A final advantage is that no molar mass regulators such as tert-dodecyl mercaptan which are, firstly, difficult to remove and, secondly, have unpleasant odors need to be added during the polymerization.

The polymer particles can be obtained as such from the initially obtained aqueous dispersions by removal of the water and, if necessary, of the organic solvent(s). Numerous customary methods are suitable for removing the water and, if necessary, the organic solvent(s), for example filtration, spray drying or evaporation. The polymers obtained in this way have a good morphology and a high bulk density.

The particle size can be determined using light scattering methods. An overview may be found in D. Distler "WäBrige Polymerdispersionen", Wiley-VCH Verlag, $1^{st}$ edition, 1999, chapter 4.

The dispersions obtained according to the present invention can be used advantageously in numerous applications, for example paper applications such as paper coating or surface sizing, also paints and varnishes, building chemicals, adhesives raw materials, molded foams, textile and leather applications, coatings on the reverse side of carpets, mattresses or pharmaceutical applications.

The following examples illustrate the invention.
General Preliminary Remarks:

All work was carried out in the absence of air and moisture using standard Schlenk techniques. Apparatus and chemicals were prepared accordingly. The polymer viscosity was determined in accordance with ISO 1628-3, and the molar masses were determined by means of GPC. For the GPC studies, the following conditions based on DIN 55672 were selected: solvent: 1,2,4-trichlorobenzene, flow: 1 ml/min, temperature: 140° C., calibration: PE standards, instrument: Waters 150 C. The number of methyl groups was determined by means of IR spectroscopy.

The following abbreviations are employed: PE=polyethylene, t-Bu: tert-butyl, Me=$CH_3$, Ph=$C_6H_5$, i-Pr=isopropyl, o-Tol=ortho-tolyl, 1. Preparation of the Ligands of the Invention:
General Method:

Equimolar amounts of the appropriate salicylaldehydes and the amino azoles were dissolved in as little methanol as possible and admixed with 0.5 ml of formic acid, and the mixture was subsequently stirred at room temperature for 12 hours. In most cases, the product could be isolated in analytically pure form by filtering off the precipitate formed and washing a number of times with methanol. In the case of the compounds 1.1, 1.3, 1.4 and 1.5, the reaction mixture was evaporated on a rotary evaporator and subsequently purified by column chromatography (silica gel Merck 60®, eluant: hexane/ether 3:2).

Table 1: Substitution Pattern of Selected Ligands According to the Present Invention

TABLE 1

1.1 to 1.16

| Example | $R^3$ | $R^5$ | $R^6$ | $R^7$ | $R^8$ | $R^9$ |
|---|---|---|---|---|---|---|
| 1.1 | H | H | Me | H | H | Me |
| 1.2 | H | H | Ph | H | H | Ph |
| 1.3 | H | H | Me | H | H | i-Pr |
| 1.4 | H | H | Me | H | H | Ph |
| 1.5 | H | H | Me | H | H | o-Tol |
| 1.6 | H | H | Ph | Ph | H | Ph |
| 1.7 | H | H | Me | H | —CH=CH—CH=CH— | |
| 1.8 | H | H | —CH=CH—CH=CH— | | —CH=CH—CH=CH— | |
| 1.9 | t-Bu | t-Bu | Me | H | H | Me |
| 1.10 | t-Bu | t-Bu | Ph | H | H | Ph |
| 1.11 | t-Bu | t-Bu | Me | H | H | i-Pr |
| 1.12 | t-Bu | t-Bu | Me | H | H | Ph |
| 1.13 | t-Bu | t-Bu | Me | H | H | o-Tol |
| 1.14 | t-Bu | t-Bu | Ph | Ph | H | Ph |
| 1.15 | t-Bu | t-Bu | Me | H | —CH=CH—CH=CH— | |
| 1.16 | t-Bu | t-Bu | —CH=CH—CH=CH— | | —CH=CH—CH=CH— | |

Analytical data for the compounds 1.1 to 1.16:

1.1: light-yellow powder, yield 55% of theory, m.p. 43–45° C., $C_{13}H_{14}N_2O$. IR(KBr): 2938 w, 2898 w, 1622 s, 1609 m, 1588 w, 1528 m, 1458 w, 1451 w, 1398 s, 1358 m, 1327 w, 1285 s, 1259 s, 1184 w, 808 m, 781 m, 767 m, 746 s, 723 s, 555 m, 476 w cm$^{-1}$. $^1$H NMR (CDCl$_3$, δ): 2.30 (6H, s, CH$_3$); 5.86 (2H, s, pyrrole); 6.93–7.40 (4H, m, phenyl); 8.45 (1H, s, imine); 11.24 (1H, s, OH). $^{13}$C NMR (CDCl$_3$, δ): 13.0 (CH$_3$), 105.7, 117.1 (pyrrole), 117.3, 119.6, 125.4, 132.0, 132.9 (phenyl), 159.3 (imine), 160.2 (phenol).

1.2: light-yellow powder, yield: 25% of theory, m.p. 122° C., $C_{23}H_{18}N_2O$. IR(KBr): 3058 w, 1622 s, 1601 s, 1568 m, 1487 s, 1458 m, 1451 m, 1387 w, 1317 w, 1304 m, 1273 s, 1225 w, 1194 m, 1151 w, 1034 w, 984 m, 918 s, 901 m, 820 m, 756 s, 737 s, 696 s, 480 m cm$^{-1}$. $^1$H NMR (CDCl$_3$, δ): 6.42 (2H, s, pyrrole); 6.70–7.51 (14H, m, phenyl); 8.04 (1H, s, imine); 10.83 (1H, s, OH). $^{13}$C NMR (CDCl$_3$, δ): 109.4, 116.7 (pyrrole), 117.2, 119.5, 127.0, 128.4, 128.7, 132.0, 132.1, 132.3, 133.0 (phenyl), 159.0 (imine), 164.2 (phenol).

1.3: light-yellow oil, yield: 36% of theory, $C_{15}H_{18}N_2O$. MS(EI): m/e 242 (M$^+$, 56%), 227 (M$^+$-CH$_3$, 100%). IR(KBr): 2965 m, 2929 m, 1622 s, 1605 s, 1570 w, 1491 m, 1460 w, 1402 m, 1383 w, 1302 m, 1279 s, 1153 s, 1107 w, 1034 m, 997 w, 972 w, 906 m, 816 m, 754 s, 584 m, 480 m cm$^{-1}$. $^1$H NMR (CDCl$_3$, δ): 1.26 (6H, d J=6.78 Hz, CH(CH$_3$)$_2$); 2.33 (3H, s, CH$_3$); 3.06 (1H, septet J=6.78 Hz, CH(CH$_3$)$_2$); 5.90 (1H, m J=0.75 Hz, pyrrole); 5.92 (1H, m J=0.75 Hz, pyrrole), 6.97–7.44 (4H, m, phenyl); 8.50 (1H, s, imine); 11.32 (1H, s, OH). $^{13}$C NMR (CDCl$_3$, δ): 13.3 (CH$_3$), 22.4 (CH(CH$_3$)$_2$), 25.7 (CH(CH$_3$)$_2$), 101.4, 106.4, 116.9 (pyrrole), 117.3, 119.6, 123.6, 132.1, 133.1 (phenyl), 137.9 (pyrrole), 159.4 (imine), 161.9 (phenol).

1.4: light-yellow powder, yield: 15% of theory, m.p. 66–69° C., $C_{18}H_{16}N_2O$. MS(EI): m/e 276 (M$^+$, 58%), 156 (M$^+$-HOC$_6$H$_4$CN, 100%). IR(KBr): 3060 w, 2923 w, 1622 s, 1605 s, 1570 w, 1516 m, 1491 m, 1474 m, 1445 w, 1395 m, 1292 s, 1271 s, 1188 w, 1153 m, 1074 w, 1034 m, 974 w, 903 w, 818 w, 750 s, 729 m, 698 s, 603 w, 509 w, 478 w cm$^{-1}$. $^1$H NMR (CDCl$_3$, δ): 2.35 (3H, d J=1.14 Hz, CH$_3$); 5.99 (1H, d×d J=1.14 Hz, J=3.78 Hz, pyrrole); 6.22 (1H, d J=3.78 Hz, pyrrole), 6.78–7.48 (9H, m, phenyl); 8.07 (1H, s, imine); 11.13 (1H, s, OH). $^{13}$C NMR (CDCl$_3$, δ): 12.5 (CH$_3$), 106.1, 109.4, 116.8 (pyrrole), 117.2, 119.5, 123.3, 126.5, 127.8, 128.7, 129.2, 132.0, 132.4, 132.9 (phenyl, pyrrole), 159.2 (imine), 162.7 (phenol).

1.5: light-yellow oil, yield: 95% of theory, $C_{19}H_{18}N_2O$. MS(EI): m/e 290 (M$^+$, 100%), 170 (M$^+$-HOC$_6$H$_4$CN, 51%). IR(KBr): 3062 w, 2923 w, 1622 s, 1607 s, 1572 w, 1522 w, 1489 m, 1472 w, 1458 w, 1395 w, 1356 w, 1290 s, 1283 s, 1269 s, 1186 w, 1153 m, 1122 w, 1034 w, 958 w, 820 w, 754 s, 725 m, 607 w, 478 w cm$^{-1}$. $^1$H NMR (CDCl$_3$, δ): 2.14 (3H, s, CH$_3$); 2.40 (3H, s, CH$_3$); 6.02 (1H, m J=3.78 Hz, pyrrole); 6.11 (1H, d J=3.78 Hz, pyrrole), 6.72–7.36 (8H, m, phenyl); 7.86 (1H, s, imine); 11.13 (1H, s, OH). $^{13}$C NMR (CDCl$_3$, δ): 12.5 (CH$_3$), 20.0 (CH$_3$), 105.3, 109.5 (pyrrole), 117.0, 119.4, 126.2, 127.5, 128.1, 128.6, 130.5, 130.7, 131.7, 132.4, 132.6, 136.9 (phenyl, pyrrole), 157.7 (imine), 158.8 (phenol).

1.6: yellow powder, yield: 72% of theory, m.p. 173–175° C., $C_{29}H_{22}N_2O$. MS(EI): m/e 414 (M$^+$, 100%), 294 (M$^+$-HOC$_6$H$_4$CN, 84%). IR(KBr): 3052 w, 1616 s, 1605 s, 1572 m, 1503 m, 1483 s, 1468 m, 1451 m, 1387 w, 1317 m, 1300 s, 1271 s, 1200 m, 1151 m, 1028 m, 964 m, 910 m, 837 w, 808 s, 764 s, 696 s, 673 m, 480 m cm$^{-1}$. $^1$H NMR (CDCl$_3$, δ): 6.57 (1H, s, pyrrole); 6.68–7.50 (19H, m, phenyl); 7.91 (1H, s, imine); 10.61 (1H, s, OH). $^{13}$C NMR (CDCl$_3$, δ): 110.1 (pyrrole), 116.7, 117.1, 119.4, 122.7, 125.9, 127.2, 127.8, 128.1, 128.2, 128.3, 128.7, 128.8, 130.9, 131.0, 131.3, 131.8, 132.0, 132.9, 135.3, 136.9 (phenyl, pyrrole), 158.8 (imine), 163.3 (phenol).

1.7: light-yellow powder, yield: 78% of theory, m.p. 150° C. (decomposition), $C_{16}H_{14}N_2O$. MS(EI): m/e 250 (M$^+$, 100%), 130 (M$^+$-HOC$_6$H$_4$CN, 91%). IR(KBr): 3048 w, 1622 s, 1613 s, 1589 s, 1568 m, 1454 s, 1379 w, 1354 m, 1329 s, 1296 s, 1267 s, 1238 m, 1153 m, 1034 w, 787 m, 756 s, 740 s, 731 s, 712 m, 559 w, 544 m, 474 w cm$^{-1}$. $^1$H NMR (CDCl$_3$, δ): (2 rotamers in the ratio 0.8:1) 2.30 (3H, s, CH$_3$); 2.52 (3H, s, CH$_3$); 6.14 (1H, s, indole); 6.35 (1H, s, indole; 6.85–7.64 (16H, m, phenyl); 8.96 (1H, s, imine); 8.97 (1H, s, imine); 11.12 (1H, s, OH); 11.20 (1H, s, OH). $^{13}$C NMR (CDCl$_3$, δ): 10.7, 12.9 (CH$_3$), 101.0, 109.5, 109.8, 111.0, 116.2, 117.3, 117.4, 117.5, 119.7, 120.6, 121.0, 121.2, 122.1, 122.3, 127.5, 127.8, 128.0, 128.3, 129.4, 131.6, 131.8, 132.2, 132.4, 132.7, 133.6, 136.0 (phenyl, indole), 155.8, 157.6 (imine), 158.8, 158.9 (phenol).

1.8: light-yellow powder, yield: 68% of theory, m.p. 148° C., $C_{19}H_{14}N_2O$. IR(KBr): 3046 w, 1622 m, 1593 w, 1483 s, 1452 s, 1445 w, 1412 w, 1333 w, 1314 m, 1302 s, 1265 m, 1215 m, 1202 w, 1155 w, 941 m, 798 m, 740 s, 715 s, 696 m, 580 w, 542 m, 478 w cm$^{-1}$. $^1$H NMR (CDCl$_3$, δ): 6.96–8.06 (12H, m, phenyl); 9.03 (1H, s, imine); 11.29 (1H, s, OH). $^{13}$C NMR (CDCl$_3$, δ): 109.9, 117.3, 117.7, 119.7, 120.4, 121.3, 122.6, 126.6, 131.4, 132.3, 137.6 (phenyl), 154.7 (imine), 158.7 (phenol).

1.9: light-yellow powder, yield: 45% of theory, m.p. 133° C., $C_{21}H_{30}N_2O$. MS(EI): m/e 326 (M$^+$, 100%), 311 (M$^+$-CH$_3$, 37%), 216 (M$^+$-Me$_2$C$_4$H$_2$N, 40%). IR(KBr): 3006 w, 2952 m, 2911 m, 1609 s, 1588 w, 1526 m, 1468 s, 1439 s, 1391 m, 1360 s, 1283 s, 1250 s, 1171 s, 968 m, 955 m, 874 s, 816 w, 771 s, 748 s, 737 s, 644 w, 513 w cm$^{-1}$. $^1$H NMR (CDCl$_3$, δ): 1.34 (9H, s, C(CH$_3$)$_3$); 1.49 (9H, s, C(CH$_3$)$_3$); 2.31 (6H, s, CH$_3$); 5.86 (2H, s, pyrrole); 7.12 (1H, d J=2.25 Hz, phenyl); 7.49 (1H, d J=2.64 Hz, phenyl); 8.47 (1H, s, imine); 11.66 (1H, s, OH). $^{13}$C NMR (CDCl$_3$, δ): 12.9 (CH$_3$), 29.4, 31.4 (C(CH$_3$)$_3$), 34.2, 35.2 (C(CH$_3$)$_3$), 105.2, 116.1 (pyrrole), 125.3, 126.6, 128.1, 137.2, 141.2 (phenyl), 156.6 (imine), 162.7 (phenol).

1.10: light-yellow powder, yield: 63% of theory, m.p. 137° C., $C_{31}H_{34}N_2O$. MS(EI): m/e 450 (M$^+$, 16%), 250 (100%), 219 (M$^+$-Ph$_2$C$_4$H$_2$N, 34%), 130 (70%). IR(KBr): 3031 w, 2954 m, 2909 w, 1609 s, 1603 s, 1582 m, 1476 m, 1462 s, 1449 s, 1435 s, 1393 m, 1362 m, 1315 w, 1300 m, 1269 s, 1250 w, 1175 m, 972 w, 771 m, 758 s, 750 s, 700 s, 507 w cm$^{-1}$. $^1$H NMR (CDCl$_3$, δ): 1.20 (9H, s, C(CH$_3$)$_3$); 1.44 (9H, s, C(CH$_3$)$_3$); 6.42 (2H, s, pyrrole); 6.59 (1H, d J=2.28 Hz, phenyl); 7.23–7.54 (11H, m, phenyl); 8.06 (1H, s, imine); 11.34 (1H, s, OH). $^{13}$C NMR (CDCl$_3$, δ): 29.4, 31.3 (C(CH$_3$)$_3$), 34.0, 35.1 (C(CH$_3$)$_3$), 108.9, 115.9 (pyrrole), 126.7, 126.8, 128.2, 128.3, 128.6, 132.1, 136.9, 141.0 (phenyl), 156.5 (imine), 166.7 (phenol).

1.11: light-yellow powder, yield: 85% of theory, m.p. 134° C., $C_{23}H_{34}N_2O$. MS(EI): m/e 354 (M$^+$, 75%), 339 (M$^+$-CH$_3$, 100%). IR(KBr): 3006 w, 2961 m, 2942 m, 2871 w, 1611 s, 1588 w, 1520 w, 1472 s, 1456 m, 1439 s, 1398 s, 1383 m, 1362 w, 1308 m, 1273 s, 1259 m, 1250 s, 1232 w, 1173 s, 1001 w, 758 s, 729 s, 511 w cm$^{-1}$. $^1$H NMR (CDCl$_3$, δ): 1.23 (6H, d J=6.78 Hz, CH(CH$_3$)$_2$); 1.33 (9H, s, C(CH$_3$)$_3$); 1.48 (9H, s, C(CH$_3$)$_3$); 2.31 (3H, s, CH$_3$); 3.04 (1H, septet J=6.78 Hz, CH(CH$_3$)$_2$); 5.86 (1H, m, pyrrole); 5.90 (1H, m, pyrrole); 7.12 (1H, d J=2.25 Hz, phenyl); 7.50 (1H, d J=2.25 Hz, phenyl); 8.49 (1H, s, imine); 11.67 (1H, s, OH). $^{13}$C NMR (CDCl$_3$, δ): 13.1 (CH$_3$), 22.5 (CH(CH$_3$)$_2$), 25.7 (CH(CH$_3$)$_2$), 29.4, 31.4 (C(CH$_3$)$_3$), 34.2, 35.2 (C(CH$_3$)$_3$), 101.0, 105.7, 116.1 (pyrrole), 123.7, 126.6, 128.3, 137.3, 137.7, 141.2 (phenyl, pyrrole), 156.7 (imine), 164.5 (phenol).

1.12: light-yellow powder, yield: 57% of theory, m.p. 157° C., $C_{26}H_{32}N_2O$. MS(EI): m/e 388 (M$^+$, 94%), 373 (M$^+$-CH$_3$, 14%), 219 (47%), 156 (HO(t-Bu)$_2$C$_6$H$_2$CN$^+$, 100%). IR(KBr): 3006 w, 2963 w, 2869 w, 1611 s, 1582 s, 1516 m, 1464 m, 1435 s, 1391 s, 1360 m, 1306 m, 1269 m, 1250 m, 1202 s, 1169 s, 1028 m, 933 w, 883 w, 848 w, 773 m, 762 s, 742 w, 717 w, 692 s, 536 w cm$^{-1}$. $^1$H NMR (CDCl$_3$, δ): 1.24 (9H, s, C(CH$_3$)$_3$); 1.46 (9H, s, C(CH$_3$)$_3$); 2.38 (3H, s, CH$_3$); 6.01 (1H, m J=3.78 Hz, pyrrole); 6.26 (1H, m J=3.78 Hz, pyrrole); 6.76 (1H, m, phenyl); 7.17–7.43 (6H, m, phenyl); 8.17 (1H, s, imine); 11.54 (1H, s, OH). $^{13}$C NMR (CDCl$_3$, δ): 12.6 (CH$_3$), 29.4, 31.3 (C(CH$_3$)$_3$), 34.1, 35.2 (C(CH$_3$)$_3$), 106.0, 108.8, 116.0 (pyrrole), 126.3, 126.6, 127.7, 128.1, 128.6, 128.9, 129.0, 132.5, 137.0, 141.1 (phenyl, pyrrole), 156.5 (imine), 164.7 (phenol).

1.13: yellow powder, yield: 88% of theory, m.p. 164° C., $C_{27}H_{34}N_2O$. MS(EI): m/e 402 (M$^+$, 44%), 362 (100%), 130 (32%). IR(KBr): 3015 w, 2963 s, 2909 w, 1613 m, 1586 w, 1470 m, 1435 s, 1395 w, 1360 s, 1288 s, 1281 s, 1250 m, 1175 w, 958 w, 876 w, 816 w, 764 s, 758 s, 723 m, 712 w, 646 m, 623 w, 453 w cm$^{-1}$. $^1$H NMR (CDCl$_3$, δ): 1.21 (9H, s, C(CH$_3$)$_3$); 1.45 (9H, s, C(CH$_3$)$_3$); 2.15 (3H, s, CH$_3$); 2.40 (3H, s, CH$_3$); 6.01 (1H, m J=3.78 Hz, pyrrole); 6.11 (1H, m J=3.78 Hz, pyrrole); 6.51 (1H, m J=2.75 Hz, phenyl); 7.16–7.37 (5H, m, phenyl); 7.86 (1H, s, imine); 11.44 (1H, s, OH). $^{13}$C NMR (CDCl$_3$, δ): 12.5, 20.1 (CH$_3$), 29.4, 31.3 (C(CH$_3$)$_3$), 34.0, 35.1 (C(CH$_3$)$_3$), 105.5, 109.0, 116.2 (pyrrole), 126.1, 126.3, 127.5, 127.8, 128.4, 130.5, 130.8, 132.7, 136.7, 137.0, 140.9 (phenyl, pyrrole), 156.0 (imine), 159.9 (phenol).

1.14: light-yellow powder, yield: 90% of theory, m.p. 164° C., $C_{43}H_{38}N_2O$. IR(KBr): 3058 w, 2957 m, 2907 w, 1609 s, 1582 m, 1481 s, 1466 m, 1452 m, 1437 s, 1391 w, 1362 w, 1317 w, 1302 m, 1273 m, 1252 s, 1202 w, 1177 m, 1028 w, 802 m, 766 s, 702 s, 684 w, 501 w cm$^{-1}$. $^1$H NMR (CDCl$_3$, δ): 1.18 (9H, s, C(CH$_3$)$_3$); 1.40 (9H, s, C(CH$_3$)$_3$); 6.51 (1H, m J=2.25 Hz, phenyl); 6.62 (1H, s, pyrrole); 7.10–7.56 (16H, m, phenyl); 7.97 (1H, s, imine); 11.13 (1H, s, OH). $^{13}$C NMR (CDCl$_3$, δ): 29.3, 31.3 (C(CH$_3$)$_3$), 34.0, 35.1 (C(CH$_3$)$_3$), 109.5 (pyrrole), 115.9, 122.4, 125.8, 126.6, 127.0, 127.5, 128.0, 128.1, 128.2, 128.3, 128.6, 128.7, 130.8, 131.1, 131.4, 131.9, 135.6, 136.8, 140.9 (phenyl, pyrrole), 156.3 (imine), 165.7 (phenol).

1.15: light-yellow powder, yield: 83% of theory, m.p. 126° C., $C_{24}H_{30}N_2O$. MS(EI): m/e 362 (M$^+$, 100%), 347 (M$^+$-CH$_3$, 18%), 130 (33%). IR(KBr): 3050 w, 2954 s, 2907 w, 2869 w, 1609 m, 1589 w, 1476 s, 1447 s, 1393 w, 1381 w, 1362 m, 1333 m, 1298 s, 1267 w, 1250 s, 1236 s, 1178 m, 1132 m, 766 s, 737 s, 725 s, 708 m, 528 w cm$^{-1}$. $^1$H NMR (CDCl$_3$, δ): 1.37 (9H, s, C(CH$_3$)$_3$); 1.51 (9H, s, C(CH$_3$)$_3$); 2.54 (3H, s, CH$_3$); 6.33 (1H, indole); 7.12–7.63 (6H, m, phenyl); 8.97 (1H, s, imine); 11.58 (1H, s, OH). $^{13}$C NMR (CDCl$_3$, δ): 12.92 (CH$_3$), 29.4, 31.5 (C(CH$_3$)$_3$), 34.2, 35.2 (C(CH$_3$)$_3$), 100.4 109.6, 116.6, 120.5, 120.9, 121.8, 126.3, 127.6, 132.4, 135.9, 137.1, 141.3 (phenyl, indole), 156.1 (imine), 158.7 (phenol).

1.16: light-yellow powder, yield: 66% of theory, m.p. 200° C., $C_{27}H_{30}N_2O$. MS(EI): m/e 398 (M$^+$, 60%), 383 (M$^+$-CH$_3$, 15%), 167 (M$^+$-HO(t-Bu)$_2$C$_6$H$_2$CN, 100%). IR(KBr): 3062 w, 2952 m, 2907 w, 2869 w, 1624 w, 1603 m, 1483 s, 1449 s, 1389 w, 1362 m, 1321 w, 1302 s, 1250 w, 1215 m, 1204 w, 1177 m, 920 m, 806 m, 767 m, 739 s, 713 s, 698 s, 684 w, 644 w, 418 w cm$^{-1}$. $^1$H NMR (CDCl$_3$, δ): 1.38 (9H, s, C(CH$_3$)$_3$); 1.54 (9H, s, C(CH$_3$)$_3$); 7.20–8.09 (10H, m, phenyl); 9.12 (1H, s, imine); 11.72 (1H, s, OH). $^{13}$C NMR (CDCl$_3$, δ): 29.5, 31.5 (C(CH$_3$)$_3$), 34.3, 35.2 (C(CH$_3$)$_3$), 109.8, 116.7, 120.4, 121.0, 122.4, 126.2, 126.5, 127.5, 137.2, 137.7, 141.4 (phenyl, indole), 156.0 (imine), 157.7 (phenol).

2. Synthesis of the beta(pyrrolimino)enolate-nickel complexes:

General Method:

The beta(pyrrolimino)enols 1.1. to 1.16 were dissolved in THF and deprotonated using an equimolar amount of n-butyllithium at −80° C. After warming to room temperature, the solvent was taken off and the residue was dissolved in benzene. The reaction solution was subsequently admixed with one equivalent of Ni(PPh$_3$)$_2$PhCl and stirred at room temperature for 12 hours. The lithium chloride formed was separated off by filtration through Celite® and the reaction solution was subsequently evaporated and the product was precipitated by addition of petroleum ether. Washing a number of times with petroleum ether and methanol gave an analytically pure product.

TABLE 2

Substitution pattern of selected complexes according to the present invention 2.1 to 2.16

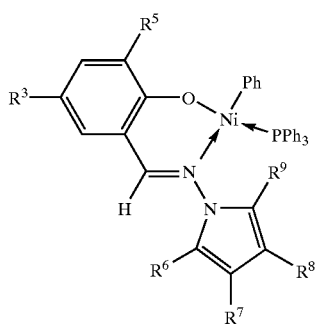

| Example | $R^3$ | $R^5$ | $R^6$ | $R^7$ | $R^8$ | $R^9$ |
|---|---|---|---|---|---|---|
| 2.1 | H | H | Me | H | H | Me |
| 2.2 | H | H | Ph | H | H | Ph |
| 2.3 | H | H | Me | H | H | i-Pr |
| 2.4 | H | H | Me | H | H | Ph |
| 2.5 | H | H | Me | H | H | o-Tol |
| 2.6 | H | H | Ph | Ph | H | Ph |
| 2.7 | H | H | Me | H | —CH=CH—CH=CH— | |
| 2.8 | H | H | —CH=CH—CH=CH— | | —CH=CH—CH=CH— | |
| 2.9 | t-Bu | t-Bu | Me | H | H | Me |
| 2.10 | t-Bu | t-Bu | Ph | H | H | Ph |
| 2.11 | t-Bu | t-Bu | Me | H | H | i-Pr |
| 2.12 | t-Bu | t-Bu | Me | H | H | Ph |
| 2.13 | t-Bu | t-Bu | Me | H | H | o-Tol |
| 2.14 | t-Bu | t-Bu | Ph | Ph | H | Ph |
| 2.15 | t-Bu | t-Bu | Me | H | —CH=CH—CH=CH— | |
| 2.16 | t-Bu | t-Bu | —CH=CH—CH=CH— | | —CH=CH—CH=CH— | |

Analytical data for the novel complexes 2.1 to 2.16

2.1: yellow powder, yield: 54% of theory, m.p. 158° C., $C_{37}H_{33}N_2NiOP$. IR(KBr): 3050 w, 2913 w, 1611 s, 1578 s, 1562 m, 1528 s, 1466 m 1441 s, 1368 w, 1341 w, 1146 m, 1128 w, 1097 m, 1020 w, 931 m, 742 s, 727 s, 704 s, 694 s, 551 m, 532s, 509 m, 495 m cm$^{-1}$. $^1$H NMR ($C_6D_6$, δ): 2.32 (6H, s, $CH_3$), 5.60 (2H, s, pyrrole), 6.32–7.77 (25H, m, phenyl, imine). $^{13}$C NMR ($C_6D_6$, δ): 12.6 ($CH_3$), 103.1 (pyrrole), 114.7, 117.4, 122.3, 123.3, 124.4, 125.2, 128.1, 128.8, 129.8, 131.2, 131.8, 132.3, 132.5, 134.2, 134.6, 134.7, 135.4, 137.4, 145.4, 146.1, 167.7, 170.2 (phenyl, pyrrole, imine). $^{31}$P NMR ($C_6D_6$, δ): 26.3.

2.2: orange powder, yield: 78% of theory, m.p. 275–280° C. (decomposition), $C_{47}H_{37}N_2NiOP$. IR(KBr): 3054 w, 1611 s, 1574 m, 1564 w, 1526 m, 1481 w, 1468 m, 1437 s, 1371 w, 1342 w, 1186 w, 1146 w, 1111 w, 1097 m, 756 s, 740 s, 729 s, 694 s, 542 w, 530 m, 509 s, 499 s cm$^{-1}$. $^1$H NMR ($C_6D_6$, δ): 6.23 (2H, s, pyrrole); 6.27–8.00 (35H, m, phenyl). $^{13}$C NMR ($C_6D_6$, δ): Owing to paramagnetic effects and the low solubility of the compound, no evaluation was possible. $^{31}$P NMR ($C_6D_6$, δ): 26.4.

2.3: yellow powder, yield: 58% of theory, m.p. 162° C., $C_{39}H_{37}N_2NiOP$. IR(KBr): 3054 w, 2959 w, 2923 w, 1611 s, 1578 s, 1562 m, 1530 m, 1466 m, 1443 m, 1368 w, 1342 m, 1223 m, 1204 w, 1146 m, 1095 m, 1020 m, 935 m, 750 s, 727 s, 692 s, 569 w, 530 s, 509 m, 495 m cm$^{-1}$. $^1$H NMR ($C_6D_6$, δ): 1.36 (3H, d J=6.67 Hz, $CH(CH_3)_2$); 1.57 (3H, d J=6.67 Hz, $CH(CH_3)_2$); 2.57 (3H, s, $CH_3$); 3.86 (1H, septet J=6.67 Hz, $CH(CH_3)_2$); 5.83 (1H, m, pyrrole); 5.90 (1H, m, pyrrole), 6.50–8.19 (25H, m, phenyl, imine). $^{13}$C NMR ($C_6D_6$, δ): 12.0 ($CH_3$), 21.1, 25.1, 25.7 ($CH(\underline{C}H_3)_2$), 99.0, 102.6 (pyrrole), 114.2, 116.6, 121.6, 122.6, 123.4, 124.8, 129.2, 130.5, 131.1, 133.5, 134.0, 134.1, 134.8, 135.4, 136.8, 167.0, 170.1 (phenyl, pyrrole, imine). $^{31}$P NMR ($C_6D_6$, δ): 26.0.

2.4: orange powder, yield: 55% of theory, m.p. 145° C., $C_{42}H_{35}N_2NiOP$. IR(KBr): 3054 w, 1609 s, 1572 s, 1562 m, 1526 m, 1514 s, 1464 m, 1439 m, 1341 w, 1204 w, 1194 w, 1180 w, 1146 m, 1121 m, 1097 m, 758 m, 739 s, 727 s, 692 s, 542 m, 532 m, 509 w cm$^{-1}$. $^1$H NMR ($C_6D_6$, δ): 2.27 (3H, s, $CH_3$); 5.76 (2H, s, pyrrole); 6.25–8.50 (30H, m, phenyl, imine). $^{13}$C NMR ($C_6D_6$, δ): 12.7 ($CH_3$), 104.7, 106.0 (pyrrole), 114.8, 117.3, 122.2, 123.4, 125.6, 128.8, 129.7, 129.8, 130.6, 131.1, 131.7, 132.3, 132.4, 132.5, 133.3, 134.0, 134.2, 134.3, 134.6, 134.7, 135.6, 136.9, 138.4, 145.9, 167.9, 170.5 (phenyl, pyrrole, imine). $^{31}$P NMR ($C_6D_6$, δ): 26.4.

2.5: orange powder, yield: 13% of theory, m.p. 175° C., $C_{43}H_{37}N_2NiOP$. IR(KBr): 3054 w, 1597 s, 1574 w, 1562 w, 1528 m, 1483 s, 1468 m, 1437 s, 1371 w, 1348 w, 1186 s, 1151 m, 1121 s, 1095 w, 852 w, 764 s, 719 s, 694 s, 586 w, 540 s cm$^{-1}$. $^1$H NMR ($C_6D_6$, δ): 1.97 (3H, s, $CH_3$); 2.41 (3H, s, $CH_3$); 5.66 (1H, m J=3.75 Hz, pyrrole); 6.08 (1H, m J=4.20 Hz, pyrrole); 6.28–8.33 (29H, m, phenyl, imine). $^{13}$C NMR ($C_6D_6$, δ): 12.4 ($CH_3$), 22.1 ($CH_3$), 103.8, 108.4 (pyrrole), 114.7, 117.4, 122.3, 123.5, 125.8. 126.4, 126.8, 128.1, 128.6, 129.7 (d $J_{PC}$=11.55 Hz), 131.1, 131.3, 131.5, 131.7, 132.9, 134.0, 134.1, 134.3, 134.5, 134.7, 135.5, 137.4, 144.9, 145.5, 167.7, 170.3 (phenyl, pyrrole, imine). $^{31}$P NMR ($C_6D_6$, δ): 25.0.

2.6: orange powder, m.p. 167° C., yield: 47% of theory, $C_{53}H_{41}N_2NiOP$. IR(KBr): 3052 w, 1611 s, 1572 m, 1528 w, 1503 w, 1483 w, 1466 w, 1437 s, 1342 w, 1261 w, 1204 w, 1148 m, 1095 m, 1028 m, 931 w, 802 w, 754 s, 731 m, 694 s, 530 m, 511 w cm$^{-1}$. $^1$H NMR ($C_6D_6$, δ): 6.03 (1H, m, pyrrole); 6.10–7.55 (40H, m, phenyl, imine). $^{13}$C NMR ($C_6D_6$, δ): 107.7 (pyrrole), 114.9, 116.6, 122.3, 123.5, 125.1, 125.8, 126.3, 127.0, 127.9, 128.5, 128.7, 128.8, 129.0, 129.3, 129.6, 129.7, 130.9, 131.5, 131.6, 132.0, 132.5, 133.2, 134.0, 134.1, 134.3, 134.5, 134.6, 135.7, 137.6, 137.9, 138.5, 138.8, 144.1, 144.8, 167.9, 171.8 (phenyl, pyrrole, imine). $^{31}$P NMR ($C_6D_6$, δ): 25.8.

2.7: yellow powder, yield: 54% of theory, m.p. 155° C., $C_{40}H_{33}N_2NiOP$. IR(KBr): 3052 w, 1609 m, 1564 m, 1526 m, 1481 w, 1466 m, 1454 w, 1437 w, 1337 w, 1308 w, 1148 w, 1148 w, 1121 m, 1095 m, 1020 w, 928 m, 739 s, 694 s, 542 s, 530 s, 509 m, 495 w cm$^{-1}$. $^1$H NMR ($C_6D_6$, δ): 2.02 (3H, s, $CH_3$); 5.50–7.50 (30H, m, phenyl, imine). $^{13}$C NMR ($C_6D_6$, δ): 12.1 ($CH_3$), 109.6 (pyrrole), 114.8, 119.8, 129.8, 131.7, 132.3, 134.3, 134.5, 134.7, further signals not observed because of paramagnetic effects (phenyl, pyrrole, imine). $^{31}$P NMR ($C_6D_6$, δ): 26.4.

2.8: orange powder, yield: 48% of theory, m.p. 149° C., $C_{43}H_{33}N_2NiOP$. IR(KBr): 3052 w, 1609 m, 1591 w, 1483 m, 1466 w, 1439 s, 1314 w, 1190 s, 1165 m, 1121 s, 1095 w, 1072 w, 1026 w, 997 m, 843 w, 752 s, 721 s, 696 s, 544 s, 499 m, 451 w cm$^{-1}$. $^1$H NMR ($C_6D_6$, δ): 7.01–7.83 (33H, m, phenyl, imine). $^{13}$C NMR ($C_6D_6$, δ): 125.8, 126.8, 128.4, 128.6, 128.8, 131.5, 131.6, 132.3, 132.4, 133.6, 134.0, 134.3, 134.9, 146.1, 147.4, 159.9 (carbazole, phenyl, imine). $^{31}$P NMR ($C_6D_6$, δ): 25.9.

2.9: yellow powder, yield: 54% of theory, m.p. 159° C., $C_{45}H_{49}N_2NioP$. IR(KBr): 3054 w, 2959 m, 1616 m, 1578 m, 1562 w, 1528 m, 1437 s, 1422 m, 1362 w, 1331 w, 1256 m, 1190 m, 1167 w, 1121 m, 1095 m, 750 m, 740 w, 727 s, 696 s, 540 s, 509 m, 492 w cm$^{-1}$. $^1$H NMR (C$_6$D$_6$, δ): 0.91 (9H, s, C(CH$_3$)$_3$); 1.27 (9H, s, C(CH$_3$)$_3$); 2.37 (6H, s, CH$_3$); 5.63 (2H, s, pyrrole); 6.35–7.83 (23H, m, phenyl, imine). $^{13}$C NMR (C$_6$D$_6$, δ): 12.6 (CH$_3$), 29.9, 31.4 (C(CH$_3$)$_3$), 34.0, 35.0 (C(CH$_3$)$_3$), 103.0 (pyrrole), 117.4, 122.1, 124.6, 125.1, 125.2, 130.0, 130.1, 131.6, 131.6, 131.8, 132.3, 132.4, 133.5, 134.8, 135.0, 135.2, 135.9, 136.4, 136.5, 141.9, 145.4, 146.1, 166.4, 170.6 (phenyl, pyrrole, imine). $^{31}$P NMR (C$_6$D$_6$, δ): 25.4.

2.10: orange powder, yield: 56% of theory, m.p. 170° C., C$_{55}$H$_{53}$N$_2$NiOP. IR(KBr): 3052 w, 2956 w, 1615 m, 1599 m, 1574 s, 1545 w, 1524 s, 1483 m, 1458 w, 1435 s, 1416 s, 1256 m, 1196 s, 1167 m, 1121 s, 1095 w, 758 w, 744 s, 729 s, 694 s, 546 s, 530 m, 511 w cm$^{-1}$. $^1$H NMR (C$_6$D$_6$, δ): 0.97 (9H, s, C(CH$_3$)$_3$); 1.20 (9H, s C(CH$_3$)$_3$); 6.30 (2H, s, pyrrole); 6.40–8.35 (33H, m, phenyl, imine). $^{13}$C NMR (C$_6$D$_6$, δ): 29.8, 31.2 (C(CH$_3$)$_3$), 33.8, 35.0 (C(CH$_3$)$_3$), 107–2 (pyrrole), 117.0, 121.8, 125.2, 126.3, 127.9, 128.5, 128.6, 128.7, 129.8, 131.6, 131.7, 132.3, 132.4, 132.6, 133.5, 134.8, 135.0, 135.1, 136.0, 136.9, 137.0, 142.0, 166.6, 171.7 (phenyl, pyrrole, imine). $^{31}$P NMR (C$_6$D$_6$, δ): 25.1.

2.11: orange powder, yield: 52% of theory, m.p. 158° C., C$_{47}$H$_{53}$N$_2$NiOP. IR(KBr): 3056 w, 2959 s, 2907 w, 2869 w, 1616 m, 1578 s, 1564 w, 1526 m, 1460 m, 1435 m, 1420 s, 1360 m, 1329 w, 1271 w, 1256 m, 1169 w, 1097 m, 744 m, 729 s, 532 s, 511 m, 473 w cm$^{-1}$. $^1$H NMR (C$_6$D$_6$, δ): 1.13 (9H, s, C(CH$_3$)$_3$); 1.36 (3H, d J=6.78 Hz, CH(CH$_3$)$_2$); 1.46 (9H, s, C(CH$_3$)$_3$); 1.58 (3H, d J=6.67 Hz, CH(CH$_3$)$_2$); 2.49 (3H, s, CH$_3$); 4.63 (1H, septet J=6.78 Hz, CH(CH$_3$)$_2$); 5.87 (2H, m, pyrrole); 6.57–8.19 (23H, m, phenyl, imine). $^{13}$C NMR (C$_6$D$_6$, δ): 12.4 (CH$_3$), 22.2, 25.6, 26.5 (CH(CH$_3$)$_2$), 29.9, 31.4 (C(CH$_3$)$_3$), 33.9, 35.0 (C(CH$_3$)$_3$), 99.7, 103.1 (pyrrole), 117.3, 121.9, 124.2, 128.1, 130.0, 131.1, 131.7, 132.3, 135.0, 135,2, 136.0, 136.3, 141.9, 145.0, 145.7, 166.4, 171.1 (phenyl, pyrrole, imine). $^{31}$P NMR (C$_6$D$_6$, δ): 24.4.

2.12: orange powder, yield: 38% of theory, m.p. 129° C., C$_{50}$H$_{51}$N$_2$NiOP. IR(KBr): 3050 w, 2959 m, 2948 m, 1616 m, 1578 s, 1562 w, 1524 m, 1508 m, 1458 w, 1437 s, 1418 s, 1333 w, 1271 w, 1258 w, 1437 s, 1418 s, 1333 w, 1271 w, 1258 w, 1167 m, 1097 s, 789 w, 748 s, 731 s, 692 s, 532 s, 511 s cm$^{-1}$. $^1$H NMR (C$_6$D$_6$, δ): 0.90 (9H, s, C(CH$_3$)$_3$); 1.24 (9H, s, C(CH$_3$)$_3$); 1.90 (3H, s, CH$_3$); 5.58 (1H, m J=3.78 Hz, pyrrole); 6.25 (1H, m J=3.78 Hz, pyrrole); 6.30–7.99 (28H, m, phenyl, imine). $^{13}$C NMR (C$_6$D$_6$, δ): 12.1 (CH$_3$), 29.8, 31.4 (C(CH$_3$)$_3$), 33.9, 34.9 (C(CH$_3$)$_3$), 104.5, 106.0 (pyrrole), 117.6, 121.9, 123.4, 125.8, 126.6, 127.9, 128.8, 129.8, 132.2, 131.3, 131.6, 132.2, 134.6, 134.9, 135.1, 135.9, 138.2, 142.3, 145.4, 146.1, 166.4, 170.4 (phenyl, pyrrole, imine). $^{31}$P NMR (C$_6$D$_6$, δ): 25.5.

2.13: orange powder, yield: 43% of theory, m.p. 176° C., C$_{51}$H$_{53}$N$_2$NiOP. IR(KBr): 3056 w, 2961 m, 2903 w, 1616 m, 1578 s, 1526 s, 1435 s, 1422 s, 1259 s, 1169 w, 1097 s, 1020 s, 877 w, 802 s, 744 m, 727 m, 702 s, 692 s, 532 s, 513 m, 493 m cm$^{-1}$. $^1$H NMR (C$_6$D$_6$, δ): 0.89 (9H, s, C(CH$_3$)$_3$); 1.24 (9H, s, C(CH$_3$)$_3$); 1.77 (3H, s, CH$_3$); 2.45 (3H, s, CH$_3$); 5.69 (1H, m J=3.75 Hz, pyrrole); 6.15 (1H, m J=3.75 Hz, pyrrole); 6.53–8.00 (27H, m, phenyl, imine). $^{13}$C NMR (C$_6$D$_6$, δ): 11.8 (CH$_3$), 21.9 (CH$_3$), 29.9, 31.4 (C(CH$_3$)$_3$), 33.9, 34.9 (C(CH$_3$)$_3$), 103.8, 108.1 (pyrrole), 117.6, 122.0, 125.9, 126.4, 126.8, 129.3, 129.8, 131.1, 131.2, 131.3, 131.4, 131.9, 132.1, 133.4, 134.9, 135.1, 135.7, 137.6, 142.4, 144.8, 145.4, 166.1, 170.2 (phenyl, pyrrole, imine). $^{31}$P NMR (C$_6$D$_6$, δ): 24.0.

2.14: orange powder, yield: 62% of theory, m.p. 206° C., C$_{61}$H$_{57}$N$_2$NiOP. IR(KBr): 3052 w, 2954 m, 2903 w, 1615 w, 1601 w, 1574 m, 1526 m, 1483 m, 1437 s, 1420 m, 1360 w, 1331 w, 1258 m, 1175 w, 1095 w, 764 m, 754 m, 729 s, 694 s, 542 m, 532 s, 511 m, 493 w cm$^{-1}$. $^1$H NMR (C$_6$D$_6$, δ): 0.83 (9H, s, C(CH$_3$)$_3$); 1.19 (9H, s, C(CH$_3$)$_3$); 6.34 (1H, m, pyrrole), 6.50–8.26 (38H, m, phenyl, imine). $^{13}$C NMR (C$_6$D$_6$, δ): 29.8, 31.3 (C(CH$_3$)$_3$), 33.9, 34.9 (C(CH$_3$)3), 107.6 (pyrrole), 116.6, 121.9, 122.1, 124.9, 125.7, 126.4, 127.1, 127.8, 128.5, 128.8, 129.6, 129.8, 131.5, 131.8, 132.0, 132.4, 132.6, 133.1, 134.9, 135.1, 135.9, 136.8, 137.1, 137.6, 142.1, 166.5, 171.8 (phenyl, pyrrole, imine). $^{31}$P NMR (C$_6$D$_6$, δ): 24.3.

2.15: yellow powder, yield: 57% of theory, m.p. 166° C., C$_{48}$H$_{49}$N$_2$NiOP. IR(KBr): 3052 w, 2957 w, 2869 w, 1615 m, 1578 s, 1551 w, 1528 s, 1478 w, 1458 m, 1435 s, 1422 s, 1356 w, 1331 w, 1258 m, 1175 w, 1097 m, 1020 w, 742 m, 729 s, 692 s, 530 s, 511 m, 493 w cm$^{-1}$. $^1$H NMR (C$_6$D$_6$, δ): 0.92 (9H, s, C(CH$_3$)$_3$); 1.27 (9H, s, C(CH$_3$)$_3$); 2.29 (3H, s, CH$_3$); 5.85 (1H, m, indole); 6.21–7.87 (27H, m, phenyl, imine). $^{13}$C NMR (C$_6$D$_6$, δ): 12.6 (CH$_3$), 29.9, 31.5 (C(CH$_3$)$_3$), 33.9, 35.0 (C(CH$_3$)$_3$), 97.4, 109.6 (pyrrole), 117.6, 119.7, 120.9, 121.9, 125.9, 127.8, 128.1, 128.6, 129.9, 130.0, 131.3, 131.8, 132.5, 134.1, 135.0, 135.2, 136.0, 136.4, 142.1, 145.3, 146.0, 166.8, 171.8 (phenyl, pyrrole, imine). $^{31}$P NMR (C$_6$D$_6$, δ): 26.2.

2.16: orange powder, yield: 73% of theory, m.p. 165° C., C$_{51}$H$_{49}$N$_2$NiOP. IR(KBr): 3052 w, 2956 w, 2905 w, 1616 m, 1574 s, 1528 s, 1483 w, 1449 s, 1435 w, 1422 s, 1331 w, 1317 w, 1258 w, 1234 m, 1173 m, 1095 m, 845 w, 742 s, 729 s, 719 w, 692 s, 530 s, 493 m cm$^{-1}$. $^1$H NMR (C$_6$D$_6$, δ): 0.95 (9H, s, C(CH$_3$)$_3$); 1.28 (9H, s, C(CH$_3$)$_3$); 5.63–7.99 (31H, m, phenyl, imine). $^{13}$C NMR (C$_6$D$_6$, δ): 29.9, 31.5 (C(CH$_3$)$_3$), 34.0, 35.0 (C(CH$_3$)$_3$), 109.4, 117.9, 119.1, 119.9, 120.8, 121.7, 124.2, 125.5, 128.7, 128.8, 129.9, 131.3, 132.0, 132.5, 135.0, 135.2, 136.1, 136.6, 139.9, 142.2, 143.7, 144.5, 145.9, 167.1, 172.9 (carbazole, phenyl, imine). $^{31}$P NMR (C$_6$D$_6$, δ): 26.6.

Standard method for polymerization using the complexes 2.1 to 2.16:

400 ml of toluene were placed in a 1 l steel autoclave. Equimolar amounts of the nickel complex and Ni(COD)$_2$ were added thereto. This reaction mixture was stirred at 30° C. for 30 minutes, and the autoclave was then pressurized with ethylene to a pressure of 40 bar. After 90 minutes, the reaction was stopped by venting and the polymer powder was isolated.

Details of the polymerizations may be found in Table 3.

TABLE 3

(polymerizations using nickel complexes):

| Complex | Amount (mmol) | Yield of PE (g) | eta value (dl/g) | Mw (g/mol) | Mn (g/mol) | Mw/Mn | Total CH$_3$ |
|---|---|---|---|---|---|---|---|
| 2.2 | 0.086 | 8.3 | 2.27 | 275437 | 12742 | 21.6 | 29 |
| 2.6 | 0.095 | 3.0 | 0.38 | n.d. | n.d. | n.d. | 40.6 |
| 2.7 | 0.096 | 0.7 | 1.5 | 102933 | 3902 | 26.4 | 34.5 |
| 2.10 | 0.096 | 12.0 | 0.57 | 14407 | 8012 | 1.8 | 39.7 |
| 2.11 | 0.092 | 25.0 | 0.97 | 33220 | 10884 | 3.0 | 26.1 |
| 2.14 | 0.089 | 12.3 | 0.38 | 12744 | 6873 | 1.85 | 35 |
| 2.15 | 0.087 | 25.0 | 0.1 | n.d. | n.d. | n.d. | 82 |
| C1 | 0.093 | 0.5 | 0.47 | n.d. | n.d. | n.d. | 23.7 | n.d.: not determined, C1: Ni(Me) (PPh$_3$)-{η$^2$-1-[C(H)=N(2,6-di-i-Pr-Ph)]-2-O—C$_6$H$_4$ (prepared using a method analogous to that of WO 98/42664)

We claim:
1. A complex of the formula I,

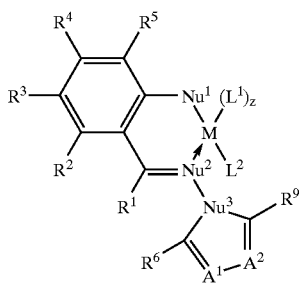

where the variables of the heteoatom containing ligand are defined as follows:
M is an element of Groups 6 to 10 of the Periodic Table of the Elements,
$Nu^1$ is selected from the group consisting of O, S and Se;
$Nu^2$, $Nu^3$ are selected from the group consisting of N and P,
$A^1$ is N or C—$R^7$ or Si—$R^7$,
$A^2$ is N or C—$R^8$ or Si—$R^8$,
$R^1$ to $R^5$ are hydrogen,
$R^6$ to $R^9$ are selected from the group consisting of (i) hydrogen, (ii) substituted or unsubstituted $C_1$–$C_8$-alkyl, (iii) substituted or unsubstituted $C_2$–$C_8$-alkenyl having from one to 4 isolated or conjugated double bonds, (iv) substituted or unsubstituted $C_3$–$C_{12}$-cycloalkyl, (v) $C_7$–$C_{13}$-aralkyl, (vi) $C_6$–$C_{14}$-aryl that is unsubstituted or monosubstituted or polysubstituted by identical or different substituents selected from the group consisting of substituted or unsubstituted $C_1$–$C_8$-alkyl, $C_3$–$C_{12}$-cycloalkyl, $C_7$–$C_{13}$-aralkyl, $C_6$–$C_{14}$-aryl, halogen, substituted or unsubstituted $C_1$–$C_6$-alkoxy, $C_6$–$C_{14}$-aryloxy, $SiR^{10}R^{11}R^{12}$ and O—$SiR^{10}R^{11}R^{12}$; and (vii) five- and six-membered nitrogen-containing heteroaryl radicals, unsubstituted or monosubstituted or polysubstituted by identical or different substituents selected from the group consisting of substituted or unsubstituted $C_1$–$C_8$-alkyl, $C_3$–$C_{12}$-cycloalkyl, $C_7$–$C_{13}$-aralkyl, $C_6$–$C_{14}$-aryl, halogen, $C_1$–$C_6$-alkoxy, $C_6$–$C_{14}$-aryloxy, $SiR^{10}R^{11}R^{12}$ and O—$SiR^{10}R^{11}R^{12}$, where adjacent radicals $R^1$ to $R^9$ are optionally joined to one another to form a 5- to 12-membered ring, said heteroatom containing ligand being in monoanionic form as a result of proton removal from the counterpart neutral ligand;
$L^1$ is an uncharged organic or inorganic ligand,
$L^2$ is an organic or inorganic anionic ligand, where $L^1$ and $L^2$ may be joined to one another by one or more covalent bonds, and
z is an integer from 1 to 3, and where $R^{10}$ to $R^{12}$ are identical or different and are selected from among the group consisting of hydrogen, $C_1$–$C_8$-alkyl, $C_3$–$C_{12}$-cycloalkyl, $C_7$–$C_{13}$-aralkyl and $C_6$–$C_{14}$-aryl.

2. The complex as claimed in claim 1 in which M is selected from the group consisting of nickel and palladium.

3. The complex as claimed in claim 1, wherein $L^1$ is selected from the group consisting of phosphines $(R^{13})_x PH_{3-x}$, amines $(R^{13})_x NH_{3-x}$, ethers $(R^{13})_2 O$, $H_2O$, alcohols $(R^{13})$ OH, pyridine, pyridine derivatives of the formula $C_5H_{5-x}$ $(R^{13})_x N$, CO, $C_1$–$C_{12}$-alkyl nitriles, $C_6$–$C_{14}$-aryl nitriles and ethylenically unsaturated double bond systems, where x is an integer ranging from 0 to 3; $L^3$ is selected from the group consisting of halide ions, amide ions $(R^{13})_{x-1}NH_{2-x}$, $C_1$–$C_6$-alkyl anions, allyl anions, benzyl anions and aryl anions, the radicals $R^{13}$ are identical or different and are selected from the group consisting of hydrogen, $C_1$–$C_8$-alkyl, $C_3$–$C_{12}$-cycloalkyl, $C_7$–$C_{13}$-aralkyl and $C_6$–$C_{14}$-aryl.

4. The complex as claimed in claim 1 in which the variables are defined as follows:
$Nu^1$ is oxygen,
$Nu^2$, $Nu^3$ are each nitrogen,
$A^1$ is N or C—$R^8$,
$A^2$ is N or C—$R^9$,
$R^1$ to $R^5$ are hydrogen, substituted or unsubstituted, $C_7$–$C_{13}$-aralkyl, $C_6$–$C_{14}$-aryl, unsubstituted or monosubstituted or polysubstituted by identical or different substituents selected from the group consisting of substituted or unsubstituted $C_1$–$C_8$-alkyl,
$R^2$ $R^6$ to $R^9$ are identical or different and are selected from the group consisting of hydrogen, substituted or unsubstituted $C_1$–$C_8$-alkyl, $C_2$–$C_8$-alkenyl that is substituted or unsubstituted and has from one to 4 isolated or conjugated double bonds; substituted or unsubstituted $C_3$–$C_{12}$-cycloalkyl, $C_7$–$C_{13}$-aralkyl, $C_6$–$C_{14}$-aryl that is unsubstituted or monosubstituted or polysubstituted by identical or different substituents selected from the group consisting of substituted or unsubstituted $C_1$–$C_8$-alkyl, halogen and $C_1$–$C_6$-alkoxy, where adjacent radicals $R^1$ to $R^9$ are optionally joined to one another to form a 5- to 12-membered ring.

5. The complex as claimed in claim 1 in which the variables are defined as follows:
$R^1$ to $R^5$ are each hydrogen,
$R^6$, $R^9$ are each $C_1$–$C_8$-alkyl, identical or different, branched or unbranched.

6. A ligand of the formula II,

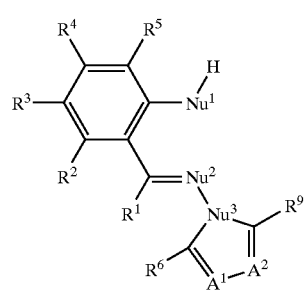

where the variables are defined as follows:
$Nu^1$ is selected from the group consisting of O, S and Se;
$Nu^2$, $Nu^3$ are selected from the group consisting of N and P.
$A^1$ is N or C—$R^7$ or Si—$R^7$,
$A^2$ is N or C—$R^8$ or Si—$R^8$,
$R^1$ to $R^5$ are hydrogen,
$R^6$ to $R^9$ are identical or different and selected from the group consisting of (i) hydrogen, (ii) substituted or unsubstituted $C_1$–$C_8$-alkyl, (iii) $C_2$–$C_8$-alkenyl that is substituted or unsubstituted and has from one to 4 isolated or conjugated double bonds, (iv) substituted or unsubstituted $C_3$–$C_{12}$-cycloalkyl, (v) $C_7$–$C_{13}$-aralkyl, $C_6$–$C_{14}$-aryl that is substituted or monosubstituted or polysubstituted by identical or different substituents selected from the group consisting of substituted or unsubstituted $C_1$–$C_8$-alkyl, $C_3$–$C_{12}$-cycloalkyl, $C_7$–$C_{13}$-aralkyl, $C_6$–$C_{14}$-aryl, halogen, substituted or unsubstituted $C_1$–$C_6$-alkoxy, $C_6$–$C_{14}$-aryloxy, $SiR^{10}R^{11}R^{12}$ and O—$SiR^{10}R^{11}R^{12}$ and five- and six-membered nitrogen-containing heteroaryl radicals that are unsubstituted or monosubstituted or polysubstituted by identical or different substituents selected from the group consisting of substituted or unsubstituted $C_1$–$C_8$-alkyl, $C_3$–$C_{12}$-cycloalkyl, $C_7$–$C_{13}$-aralkyl, $C_6$–$C_{14}$-aryl, halogen, $C_1$–$C_6$-alkoxy, $C_6$–$C_{14}$-aryloxy, $SiR^{10}R^{11}R^{12}$ and O–$SiR^{10}R^{11}R^{12}$, where adjacent radicals $R^1$ to $R^9$ are optionally joined to one another to form a 5- to 12-membered ring and where $R^{10}$ to $R^{12}$ are identical or different and are selected from the group consisting of hydrogen, $C_1$–$C_8$-alkyl, $C_3$–$C_{12}$-cycloalkyl, $C_7$–$C_{13}$-aralkyl and $C_6$–$C_{14}$-aryl.

7. A process for preparing complexes as claimed in claim 1, which comprises firstly deprotonating a ligand of the formula II by means of a base and subsequently reacting the product with from 0.2 to 5 equivalents of a metal compound $MX_4$, $MX_3$, $ML^1L^2$ or $MX_2$, where X is halogen, $C_1$–$C_8$-alkyl, $C_3$–$C_{12}$-cycloalkyl, $C_7$–$C_{13}$-aralkyl or $C_6$–$C_{14}$-aryl and $MX_2$, $MX_3$ or $MX_4$ optionally are stabilized by further uncharged ligands.

8. A process for preparing ligands as claimed in claim 6, which comprises reacting a carbonyl compound of the formula III

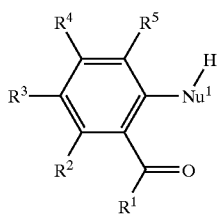

III with a compound of the formula IV

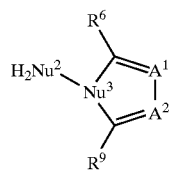

IV at a temperature ranging from −78° C. to +150° C. in the presence of a Lewis acid or a Bronsted acid.

9. A process for the polymerization or copolymerization of olefins using complexes as claimed in claim 1.

10. A process for preparing a supported catalyst for the polymerization or copolymerization of olefins, which comprises:

depositing one or more complexes as claimed in claim 1, and optionally an activator on a solid support.

11. A supported catalyst for the polymerization or copolymerization of olefins as set forth in claim 9.

12. A process for the polymerization or copolymerization of olefins in the presence of the supported catalyst as claimed in claim 10.

13. A process for the emulsion polymerization or emulsion copolymerization of ethylene or other 1-olefins and, optionally other non-1-olefins in the presence of the complex of formula I of claim 1.

14. The complex as claimed in claim 1, wherein (i) said $C_1$–$C_8$-alkyl group is methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl or n-octyl; (ii) said substituted $C_1$–$C_8$-alkyl group is a monohalogenated or polyhalogenated $C_1$–$C_8$-alkyl groups selected from the group consisting of fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl; (iii) said $C_2$–$C_8$-alkenyl vinyl, 1-alkyl, 3-alkyl, ω-butenyl, ω-pentenyl, ω-hexenyl, 1-cis-buta-1,3-dienyl or 1-cis-hexa-1,5-dienyl; (iv) said substituted $C_2$–$C_8$-alkenyl group is isopropenyl, 1-isopentyl, α-styryl, β-styryl, 1-cis-1,2-phenylethenyl or 1-trans-1,2-phenylethenyl; (v) said $C_3$–$C_{12}$-cycloalkyl group is cyclopropyl, cyclobutyl, cyclopentyl, cyclohexyl, cycloheptyl, cyclooctyl, cyclononyl, cyclodecyl, cycloundecyl or cyclododecyl; (vi) said substituted cycloalkyl group is 2-methylcyclopentyl, 3-methylcyclopentyl, cis-2,4-dimethylcyclopentyl, trans-2,4-dimethylcyclopentyl, cis-2,5-dimethylcyclopentyl, trans-2,5-dimethylcyclopentyl, 2,2,5,5-tetramethylcyclopentyl, 2-methylcyclohexyl, 3-methylcyclohexyl, 4-methylcyclohexyl, cis-2,6-dimethylcyclohexyl, trans-2,6-dimethylcyclohexyl, cis-2,6-diisopropylcyclohexyl, trans-2,6-diisopropylcyclohexyl, 2,2,6,6-tetramethylcyclohexyl, 2-methoxycyclopentyl, 2-methoxycyclohexyl, 3-methoxycyclopentyl, 3-methoxycyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,6,6-tetrachlorocyclohexyl, 2-thiomethylcyclopentyl, 2-thiomethylcyclohexyl, 3-thiomethylcyclopentyl or 3-thiomethylcyclohexyl; (vii) said $C_7$–$C_{13}$-aralkyl is a $C_7$–$C_{12}$-phenylalkyl selected from the group consisting of benzyl, 1-phenethyl, 2-phenethyl, 1-phenylpropyl, 2-phenylpropyl, 3-phenylpropyl, neophyl (1-methyl-1-phenylbutyl), 1-phenylbutyl, 2-phenylbutyl, 3-phenylbutyl and 4-phenylbutyl; (viii) said $C_6$–$C_{14}$-aryl is phenyl, 1-naphthyl, 2-naphthyl, 1-anthryl, 2-anthryl, 9-anthryl, 1-phenanthryl, 2-phenanthryl, 3-phenanthryl, 4-phenanthryl or 9-phenanthryl; (ix) said $C_6$–$C_{14}$-aryl is phenyl, 1-naphthyl, 2-naphthyl, 1-anthryl, 2-anthryl, 9-anthryl, 1-phenanthryl, 2-phenanthryl,-3-phenanthryl, 4-phenanthryl or 9-phenanthryl substituted by one or more identical or different substituents selected from the group consisting of $C_1$–$C_8$-alkyl, substituted $C_1$–$C_8$-alkyl, $C_3$–$C_{12}$-cycloalkyl, $C_7$–$C_{13}$-aralkyl, $C_6$–$C_{14}$-aryl, halogen, $C_1$–$C_6$-alkoxy, $C_6$–$C_{14}$-aryloxy, silyl groups $SiR^{10}R^{11}R^{12}$, where $R^{10}$ to $R^{12}$ arc selected independently from the group consisting of hydrogen, $C_1$–$C_8$-alkyl, benzyl and $C_6$–$C_{14}$-aryl groups or silyloxy groups $OSiR^{10}R^{11}R^{12}$ where $R^{10}$ to $R^{12}$ are selected independently from the group consisting of hydrogen, $C_1$–$C_8$-alkyl, benzyl and $C_6$–$C_{14}$-aryl; and (x) five- and six-membered nitrogen-containing heteroaryl radicals selected from the group consisting of N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl, each optionally substituted by one or more identical or different substituents selected from the group consisting of 1–C$_8$-alkyl, substituted C$_1$–C$_8$-alkyl, C$_3$–C$_{12}$-cycloalkyl, C$_7$–C$_{13}$-aralkyl, C$_6$–C$_{14}$-aryl, halogen, C$_1$–C$_6$-alkoxy, C$_6$–C$_{14}$-aryloxy, silyl groups SiR$^{10}$R$^{11}$R$^{12}$, where R$^{10}$ to R$^{12}$ are selected independently from the group consisting of hydrogen, C$_1$–C$_8$-alkyl, benzyl and C$_6$–C$_{14}$-aryl and silyloxy groups OSiR$^{10}$R$^{11}$R$^{12}$, where R$^{10}$ to R$^{12}$ are selected independently from the group consisting of hydrogen, C$_1$–C$_8$-alkyl, benzyl and C$_6$–C$_{14}$-aryl.

15. A process for the polymerization or copolymerization of olefins using complexes as claimed in claim 1, thereby producing a polyolefin product having a molecular weight distribution of at least 21.6.

16. A process for the polymerization or copolymerization of olefins in the presence of the supported catalyst as claimed in claim 10, thereby producing a polyolefin product having a molecular weight distribution of at least 21.6.

17. A process for the emulsion polymerization or emulsion copolymerization of ethylene or other 1-olefins and, optionally other non-1-olefins in the presence of the complex of formula I of claim 1, thereby producing a polyolefin product having a molecular weight distribution of at least 21.6.

18. A process for the polymerization or copolymerization of olefins using complexes as claimed in claim 1, thereby producing a polyolefin product having a molecular weight distribution of at least 3.5.

19. A process for the polymerization or copolymerization of olefins in the presence of the supported catalyst as claimed in claim 10, thereby producing a polyolefin product having a molecular weight distribution of at least 3.5.

20. A process for the emulsion polymerization or emulsion copolymerization of ethylene or other 1-olefins and, optionally other non-1-olefins in the presence of the complex of formula I of claim 1, thereby producing a polyolefin product having a molecular weight distribution of at least 3.5.

* * * * *